(12) United States Patent
Abbott et al.

(10) Patent No.: US 8,329,423 B2
(45) Date of Patent: Dec. 11, 2012

(54) DEVICE AND METHODS FOR LIQUID CRYSTAL-BASED BIOAGENT DETECTION

(75) Inventors: Nicholas L. Abbott, Madison, WI (US); Joon-Seo Park, Madison, WI (US); Sarah Teren, Madison, WI (US); David J. Beebe, Monona, WI (US); Eric A. Johnson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/011,514

(22) Filed: Jan. 21, 2011

(65) Prior Publication Data

US 2011/0183357 A1 Jul. 28, 2011

Related U.S. Application Data

(62) Division of application No. 11/555,103, filed on Oct. 31, 2006, now Pat. No. 7,910,382.

(60) Provisional application No. 60/731,824, filed on Oct. 31, 2005.

(51) Int. Cl.
*G01N 33/553* (2006.01)
(52) U.S. Cl. ........................................................ 435/7.9
(58) Field of Classification Search .................... 435/7.9
See application file for complete search history.

(56) References Cited

U.S. PATENT DOCUMENTS

| | | | |
|---|---|---|---|
| 4,513,034 A | 4/1985 | Sparer | |
| 4,597,942 A | 7/1986 | Meathrel | |
| 4,628,037 A | 12/1986 | Chagnon et al. | |
| 4,725,669 A | 2/1988 | Essex et al. | |
| 4,812,556 A | 3/1989 | Vahine et al. | |
| 4,902,106 A | 2/1990 | Dijon | |
| 5,071,526 A | 12/1991 | Pletcher et al. | |
| 5,091,318 A | 2/1992 | Anawis et al. | |
| 5,130,828 A | 7/1992 | Fergason | |
| 5,568,256 A | 10/1996 | Korner et al. | |
| 5,618,493 A | 4/1997 | Goldstein et al. | |
| 5,620,850 A | 4/1997 | Bamdad et al. | |
| 5,658,491 A | 8/1997 | Kistner | |
| 5,677,195 A | 10/1997 | Winkler et al. | |
| 5,686,018 A | 11/1997 | Demus et al. | |
| 5,712,103 A | 1/1998 | Leavitt et al. | |
| 5,940,201 A | 8/1999 | Ash et al. | |
| 6,005,668 A | 12/1999 | Held, III et al. | |
| 6,060,327 A | 5/2000 | Keen | |
| 6,097,484 A | 8/2000 | McIntosh et al. | |
| 6,159,681 A | 12/2000 | Zebala | |

(Continued)

FOREIGN PATENT DOCUMENTS

WO 03/019191 A 3/2003

(Continued)

OTHER PUBLICATIONS

PCT/US2006/060396 International Search Report, Oct. 12, 2007.

(Continued)

*Primary Examiner* — Mark Shibuya
*Assistant Examiner* — Pensee Do
(74) *Attorney, Agent, or Firm* — Quarles & Brady LLP

(57) ABSTRACT

The present invention provides liquid crystal-based devices and methods for bioagent detection. In certain aspects, the present invention is directed to devices and methods utilizing liquid crystals and membranes containing polymerized targets that can report the presence of bioagents including, but not limited to, enzymes, antibodies, and toxins.

8 Claims, 9 Drawing Sheets

U.S. PATENT DOCUMENTS

| | | |
|---|---|---|
| 6,171,802 B1 | 1/2001 | Woolverton et al. |
| 6,178,034 B1 | 1/2001 | Allemand et al. |
| 6,203,304 B1 | 3/2001 | Tonazzi et al. |
| 6,207,369 B1 | 3/2001 | Wohlstadter et al. |
| 6,277,489 B1 | 8/2001 | Abbott et al. |
| 6,284,197 B1 | 9/2001 | Abbott et al. |
| 6,288,392 B1 | 9/2001 | Abbott et al. |
| 6,291,188 B1 | 9/2001 | Meade et al. |
| 6,306,594 B1 | 10/2001 | Cozzette et al. |
| 6,383,815 B1 | 5/2002 | Potyrallo |
| 6,383,816 B1 | 5/2002 | Wirth et al. |
| 6,413,587 B1 | 7/2002 | Hawker et al. |
| 6,491,061 B1 | 12/2002 | Lopez et al. |
| 6,540,939 B1 | 4/2003 | Martin et al. |
| 6,692,699 B2 | 2/2004 | Abbott et al. |
| 6,797,463 B2 | 9/2004 | Abbott et al. |
| 6,824,837 B2 | 11/2004 | Abbott et al. |
| 2002/0004216 A1 | 1/2002 | Abbott et al. |
| 2002/0025391 A1 | 2/2002 | Angelopoulos et al. |
| 2002/0028451 A1 | 3/2002 | Abbott et al. |
| 2002/0055093 A1 | 5/2002 | Abbott et al. |
| 2002/0071943 A1 | 6/2002 | Hawker et al. |
| 2002/0142453 A1 | 10/2002 | Abbott et al. |
| 2002/0164604 A1 | 11/2002 | Abbott et al. |
| 2003/0071949 A1 | 4/2003 | Abbott et al. |
| 2003/0099993 A1 | 5/2003 | Abbott et al. |
| 2003/0180966 A1 | 9/2003 | Abbott et al. |
| 2003/0194753 A1 | 10/2003 | Abbott et al. |
| 2007/0166533 A1 | 7/2007 | Lazarev et al. |

FOREIGN PATENT DOCUMENTS

| | | |
|---|---|---|
| WO | 03/086197 A | 10/2003 |

OTHER PUBLICATIONS

Yevdokimov Y M, Double-Stranded DNA Liquid Crystalline Dispersions as Biosensing Units, Biochemical Society Transations, vol. 28, No. 2, 2000 pp. 77-81.

Skuridin S G et al., A New Approach for Creating Double-Stranded DNA Biosensors, Biosensors & Bioelectronics, vol. 11, No. 9, 1996, pp. 903-911.

Jian-She Hu et al. Mesomorphic Properties of Side-Chain Cholesteric Liquid-Crystalline Elastomers, Colloid and Polymer Science, vol. 283, No. 12, Sep. 1, 2005, pp. 1349-1355.

Cremer P S, Label-Free Detection Becomes Crystal Clear, Nature Biotechnology, vol. 22, No. 2, 2004 pp. 172-173.

Yevdokimov Yu et al., Double-Stranded Nucleic Acids in Liquid-Crystalline Dispersions as Building Blocks for Cross-Linked Supramolecular Structures, Nucleosides, Nucleotides and Nucleic Acids, vol. 19, No. 8, 2000 pp. 1355-1364.

Brake et al. "Biomolecular Interactions at Phospholipid-Decorated Surfaces of Liquid Crystals," Science, vol. 302, 2003 pp. 2094-2097.

DEVICE AND METHODS FOR LIQUID CRYSTAL-BASED BIOAGENT DETECTION

CROSS-REFERENCE TO RELATED APPLICATIONS

This application is a divisional of U.S. application Ser. No. 11/555,103, filed on Oct. 31, 2006 and issued as U.S. Pat. No. 7,910,382 on Mar. 22, 2011, which claims the benefit of U.S. Provisional Application No. 60/731,824, filed Oct. 31, 2005, both of which are incorporated by reference herein in their entirety.

STATEMENT REGARDING FEDERALLY SPONSORED RESEARCH

This invention was made with government support under N00014-14-04-1-0659 awarded by the Navy/ONR. The government has certain rights in the invention.

FIELD OF THE INVENTION

This invention relates generally to methods of analyte detection using liquid crystals. In particular, the present invention is directed to devices and methods utilizing liquid crystals and membranes containing polymerized targets that can report the presence of bioagents including, but not limited to, enzymes and antibodies.

BACKGROUND OF THE INVENTION

Most present biosensors take advantage of biologically active materials for high sensitivity and selectivity. In general, the biosensor includes a biorecognition structure (e.g., a membrane) in contact with or interrogated by a transducer. The biologically active material recognizes a particular biological molecule through a reaction, specific adsorption, or other physical or chemical process, and the transducer converts the output of this recognition into a usable signal, usually electrical or optical. Many approaches have been explored to achieve ultra-sensitive detection of bio-species. These biodetection approaches can be categorized as either an engineering-oriented approach or a biological-oriented approach. In other words, most biodetection schemes are either based on relatively complex electronic, photonic and/or electrochemical methods or more elegant biomolecular methods (e.g. enzyme linked immunosorbent assay, or ELISA) typically with an optical or spectrometry-based readout.

By way of example, one process utilizes photonics integrated on a microchip to study the interaction between the optical field and the target bio-analyte. Because most biorecognition processes occur in an aqueous ambient, this approach requires the integration of photonics, highly sensitive microelectronics and microfluidic systems on a single microchip. The use of ion-channel switches as biosensors has also been explored, but the bioelectronic interface is a delicate one. Often, when an approach promises very high sensitivity, the output signal from the biorecognition is very small, thus requiring extremely highly-sensitive on-chip microelectronics for signal amplification, processing and wireless transmission. The high demand of these approaches on system integration and high sensitivity photonics and electronics circuitry presents a big challenge to the biosensors in terms of cost, reliability and power consumption. The more biomolecular based approaches, like ELISA, are simple, but typically require a macro scale spectrometry system to quantify the output.

Therefore, it is a primary object and feature of the present invention to provide a bioagent detection device that is highly sensitive and selective, has a quick response time, and generates few false alarms.

SUMMARY OF THE INVENTION

In a first aspect, the present invention provides a liquid crystal device for detecting the presence of a bioagent in a sample. Such a device includes: (a) a liquid crystal; (b) an aqueous phase positioned such that an interface exists between the liquid crystal and the aqueous phase; and (c) a membrane containing a polymerized target of a bioagent. The membrane is located at the interface between the liquid crystal and the aqueous phase. Interaction of the bioagent with the polymerized target causes an orientation change in the liquid crystal thereby indicating the presence of the bioagent in the sample.

In certain embodiments, the bioagent is an enzyme and the target is a substrate for the enzyme. Preferred embodiments are directed to the detection of proteases, metalloproteases, and, most preferably, neurotoxins with metalloprotease activities. Accordingly, embodiments for neurotoxin detection include a substrate that is a peptide cleavable by the respective neurotoxin. For example, certain of the present devices detect the presence of botulinum toxin using as substrate a peptide cleavable by botulinum toxin (e.g., synaptosomal-associated protein 25 (SNAP-25) or a cleavable fragment thereof). In other embodiments, the enzyme detected is a neurotoxin with phospholipase $A_2$ activity and the substrate is a 1,2-diacyl-3-sn-phosphoglyceride containing an sn-2 ester bond.

In yet other embodiments, the liquid crystal device detects the presence of an antibody in a sample by using as target an antigen recognized by the respective antibody. As well, a sample may contain an antigen as a bioagent with the target then being an antibody that recognizes the antigen.

The polymerized target may be provided in a variety of forms but target molecules are preferably cross-linked by a cross-linking agent. Suitable cross-linking agents include, but not limited to, zero length cross-linkers (e.g., 1-ethyl-3-(3-dimethylaminopropyl) carbodiimide hydrochloride (EDC)); homobifunctional cross-linkers (e.g., the NHS ester dithiobis(succinimidylpropionate (DSP), the imidoester dimethyl adipimidate (DMA), sulfhydryl-reactive 1,4-Di-[3'-(2'-pyridyldithio)priopionamido]butane (DPDPB), the difluorobenzene derivative 1,5-difluoro-2,4-dinitrobenzene (DFDNB), formaldehyde, bis-epoxides, and hydrazides); heterobifunctional cross-linkers (e.g., amine reactive and sulfhydryl reactive N-succinimidyl 3-(2-pyridyldithio)propionate (SPDP), and carbonyl-reactive and sulfhydryl-reactive 4-(4-N-maleimidophenyl)butyric acid hydrazide (MPBH); and, as well, trifunctional cross-linkers (e.g., 4-azido-2-nitrophenylbiocytin-4-nitrophenyl ester). Particularly preferred cross-linking agents are adipoyl chloride and 1,4-dimaleimidobenzene.

Although the polymerized target may be provided essentially by itself at the aqueous phase/liquid crystal interface, certain alternative embodiments further comprise non-target molecules in combination with the target molecules such that target and non-target molecules are in close association, preferably cross-linked with each other. In some embodiments, the non-target molecule is a layer adsorbed or deposited at the aqueous-liquid crystal interfaces to which a target molecule is cross-linked. In preferred embodiments, the non-target molecule is a surfactant, lipid or polymer that is adsorbed at the interface. In other preferred embodiments, the non-target molecule at the interface contains a amine or carboxylic acid group that is used to form a covalent cross-link with biomolecules at the interface.

Certain devices according to the invention further include an enhancing agent present in the aqueous phase that enhances the change in orientation of the liquid crystal upon interaction of the bioagent and target. Enhancing agents useful in this regard include, but are not limited to dilauroyl phosphatidylcholine (DLPC), phospholipids (such as DPPC, DMPC), glycolipids, saturated and unsaturated lipids, fatty acids, polymers that cause homeotropic anchoring, anionic surfactants, cationic surfactants, non-ionic surfactants, zwitterionic surfactants, amphiphilic molecules that generate known orientations of liquid crystals. In general, enhancing agents that generate known orientations of liquid crystal at the aqueous-liquid crystal interface are useful for this purpose.

In one aspect of the invention, a method for preparing a liquid crystal device for detecting the presence of a bioagent in a sample is provided. Such methods include steps of: (a) dissolving a cross-linking agent into a liquid crystal; and (b) adding a target of a bioagent to an aqueous phase that contacts said liquid crystal to cause an interfacial reaction between the target and the cross-linking agent. The interaction provides a membrane containing a polymerized target at the interface of the liquid crystal, the polymerized target positioned to interact with a bioagent contacted with the membrane. Subsequent interaction between bioagent and target causes an orientation change in the liquid crystal thereby indicating the presence of the bioagent.

In yet another aspect of the invention, methods for detecting the presence of a bioagent in a sample are provided. Such methods include steps of: (a) forming a membrane containing a polymerized target for an enzyme at an interface between a liquid crystal and an aqueous phase; and (b) introducing a bioagent into the aqueous phase wherein interaction of the bioagent and polymerized target leads to a change in the orientational order of the liquid crystal. The orientational change indicates the presence of the bioagent in the sample.

In certain embodiments, the bioagent is an enzyme and the target is a substrate for the enzyme. Preferred embodiments are directed to the detection of proteases, metalloproteases and, most preferably, neurotoxins with metalloprotease activities. Accordingly, the substrate in such methods is a peptide cleavable by the neurotoxin. For example, certain methods detect the presence of botulinum toxin using as substrate a peptide cleavable by botulinum toxin (e.g., SNAP-25 or a cleavable fragment thereof). In other embodiments, the enzyme detected is a neurotoxin with phospholipase $A_2$ activity and the substrate is a 1,2-diacyl-3-sn-phosphoglyceride containing an sn-2 ester bond.

In yet other embodiments, the method according to the invention detects the presence of an antibody in a sample by using as target an antigen recognized by the respective antibody. As well, a sample may contain an antigen as a bioagent with the target then being an antibody that recognizes the antigen.

Certain methods according to the invention further include an enhancing agent present in the aqueous phase that enhances the change in orientation of the liquid crystal upon interaction of the bioagent and target. Enhancing agents useful in this regard include, but are not limited to, L-α-dilauroyl phosphatidylcholine (L-DLPC), phospholipids (such as DPPC, DMPC), glycolipids, saturated and unsaturated lipids, fatty acids, polymers that cause homeotropic anchoring, anionic surfactants, cationic surfactants, non-ionic surfactants, zwitterionic surfactants, amphiphilic molecules that generate known orientations of liquid crystals. In general, enhancing agents that generate known orientations of liquid crystal at the aqueous-liquid crystal interface are useful for this purpose.

It can be appreciated that devices and methods according to the invention permit the incorporation of widely differing targets for bioagents, including but not limited to proteins and lipids. It can also be appreciated that a variety of different interactions between bioagent and target can be detected by the invention, including, e.g., disruption, perturbation and/or degradation of target by bioagent. As well, fabrication methods according to the invention provide substrate containing membranes that can be tuned in thickness to balance the need for sensitivity and robustness.

Other objects, features and advantages of the present invention will become apparent after review of the specification, claims and drawings.

DETAILED DESCRIPTION OF THE INVENTION

I. In General

Figure 1:
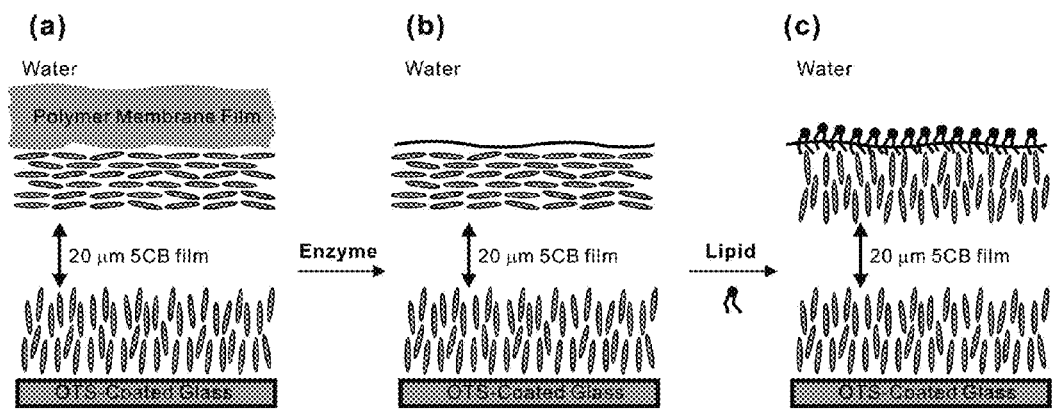
FIG. 1. Schematic representation of the enzymatic cleavage of polymer membrane film at the aqueous-5CB interface and the subsequent lipid monolayer formation.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the materials, chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

In a first aspect, the present invention provides a liquid crystal device for detecting the presence of a bioagent in a sample. Such a device includes: (a) a liquid crystal; (b) an aqueous phase positioned such that an interface exists between the liquid crystal and the aqueous phase; and (c) a membrane containing a polymerized target of a bioagent. The membrane is located at the interface between the liquid crystal and the aqueous phase. Interaction of the bioagent with the polymerized target causes an orientation change in the liquid crystal thereby indicating the presence of the bioagent in the sample.

As used herein, the term "bioagent" shall encompass a wide variety of molecules and assemblies of molecules such as viruses, bacteria, eukaryotic and prokaryotic cells to be detected in a fluid sample. Such molecules may be synthetic or natural in origin and include, but are not limited to, protein, carbohydrate, lipid, nucleic acid, and organic/inorganic small molecule entities. These molecules and assemblies may be complexes with metal ions. In certain embodiments, the bioagent is an enzyme and the target is a substrate for the bioagent. Preferred embodiments are directed to the detection proteases and metalloproteases, including neurotoxins with metalloprotease activities. Accordingly, the substrate is a peptide cleavable by said neurotoxin. For example, certain devices detect the presence of botulinum toxin using as substrate a peptide cleavable by botulinum toxin (e.g., SNAP-25 or a cleavable fragment thereof). In other embodiments, the enzyme detected is a neurotoxin with phospholipase $A_2$ activity and the substrate is a 1,2-diacyl-3-sn-phosphoglyceride containing an sn-2 ester bond. In yet other embodiments, the liquid crystal device detects the presence of an antibody in a sample by using an antigen recognized by the respective antibody.

As used herein, the term "polymerized target" refers to biomolecules (e.g., proteins, peptides, oligopeptides, lipids, peptide amphiphiles, carbohydrates, nucleic acids, or small organic/inorganic molecules, molecules that interact with biological entities including prokaryotic and eukaryotic organisms) that have been cross-linked to form interconnected molecular networks while still retaining the ability to interact with a bioagent. The term "interact" in the context of target and bioagent includes, but is not limited to, the disruption, perturbation and/or degradation of the target by the direct action of the bioagent. As described herein, polymerized targets are preferably formed by cross-linking target molecules with the aid of a cross-linking agent. The term "cross-linking agent" or "conjugation agent" shall refer to the broad family of conjugation reagents known in the art to be useful in conjugating (cross-linking) biomolecules. Cross-linking agents useful in the invention, particularly in the protein context, include, but are not limited to: zero length cross-linkers (e.g., 1-ethyl-3-(3-dimethylaminopropyl) carbodiimide hydrochloride (EDC)); homobifunctional cross-linkers (e.g., the NHS ester dithiobis(succinimidylpropionate (DSP), the imidoester dimethyl adipimidate (DMA), sulfhydryl-reactive 1,4-Di-[3'-(2'-pyridyldithio)priopionamido]butane (DPDPB), the difluorobenzene derivative 1,5-difluoro-2,4-dinitrobenzene (DFDNB), formaldehyde, bis-epoxides, and hydrazides); heterobifunctional cross-linkers (e.g., amine reactive and sulfhydryl reactive N-succinimidyl 3-(2-pyridyldithio)propionate (SPDP), and carbonyl-reactive and sulfhydryl-reactive 4-(4-N-maleimidophenyl)butyric acid hydrazide (MPBH); and, as well, trifunctional cross-linkers (e.g., 4-azido-2-nitrophenylbiocytin-4-nitrophenyl ester). Particularly preferred cross-linking agents are adipoyl chloride and 1,4-dimaleimidobenzene. Conjugation of proteins to lipids may be accomplished, e.g., via the NHS ester of a fatty acid, carbodiimide coupling, glutaraledyde coupling, DMS cross-linking, N-succinimidyl 3-(2-pyridyldithio)propionate (SPDP)-modified lipid derivatives, or succinimidyl-4-(para-maleimidophenyl)butyrate (SMPB)-modified lipid derivatives. In the antibody context, cross-linking techniques are known in the art and exemplary such techniques include NHS ester-maleimide-mediated conjugation, glutaraldehyde-mediated conjugation, reductive-amination-mediated conjugation, and disulfide exchange reactions. An extensive list of suitable cross-linking agents is presented in "Bioconjugate Techniques" by Greg T. Hermanson, Academic Press, 1996, ISBN0-12-342336-8, incorporated herein by reference.

Although the polymerized target may be provided essentially alone at the aqueous phase/liquid crystal interface, certain alternative embodiments further comprise non-target molecules in combination with the target molecules such that target and non-target molecules are in close association, preferably cross-linked with each other. "Non-target" molecules are provided in combination with target molecules but are not directly disrupted, perturbed, and/or degraded by the bioagent. Non-target molecules may be indirectly acted upon by bioagents because they are coupled to the target and, consequently, effect underlying liquid crystal orientation. In one embodiment, the non-target molecule is a spontaneously adsorbed or deposited monolayer to which a target molecule is cross-linked. Preferred classes of non-target molecule are polymers, surfactants and lipids that are assembled at the liquid crystal-aqueous interface. Non-target molecules may be provided as mixtures or combinations. A particularly preferred class of non-target molecules are lipids and surfactants that contain non-ionic groups such as ethylene glycol. A preferred embodiment of the invention involves the use of surfactants that incorporate ethylene glycol head groups such as tetraethylene glycol monotetradecyl ether (C14EG4) and 3,6,9,12,15-pentaoxanonacosanoic acid (C14EG4-$CO_2$H), and mixtures of these two compounds. A further preferred embodiment of the invention uses NHS/EDC to activate the carboxylic acid group of 3,6,9,12,15-pentaoxanonacosanoic acid to form a cross-linked network of the target and non-target molecules at the interface between the liquid crystal and aqueous phase.

Furthermore, different types of liquid crystals can be employed in the present invention, including nematic and smectic liquid crystals, and thermotropic liquid crystals, as will be evident to those skilled in the art of liquid crystals. Examples of suitable liquid crystals, include, but are not limited to, 4-cyano-4'-pentylbiphenyl (5CB), 7CB, and 8CB. A large listing of suitable liquid crystals is presented in "Handbook of Liquid Crystal Research" by Peter J. Collings and Jay S. Patel, Oxford University Press, 1997, ISBN 0-19-508442-X, incorporated herein by reference. Polymeric liquid crystals are also suitable for use in the device and methods of the present invention. Other liquid crystals are nematic liquid crystals such as E7, smectic liquid crystals, thermotropic liquid crystals, lyotropic liquid crystals, polymeric liquid crystals, cholesteric liquid crystals and ferroelectric liquid crystals. In a preferred embodiment of the present invention, the liquid crystal deposited in the device is 4-cyano-4'-pentylbiphenyl (5CB). Although various types of liquid crystal may be employed, nematic and thermotropic liquid crystals are preferred. However, smectic liquid crystals formed from 8CB are also suitable for use in the present invention. Suitable liquid crystals further include smectic C, smectic C*, blue phases, cholesteric phases, smectic A, and polymeric liquid crystals. It is further envisioned that LCs useful in the invention may further include additions of dopants such as, but not limited to, chiral dopants as described by Shitara H, et al. (*Chemistry Letters* 3: 261-262 (1998)) and Pape, M., et al. (*Molecular Crystals and Liquid Crystals* 307: 155-173 (1997)). The introduction of a dopant permits manipulation of the liquid crystal's characteristics including, but not limited to, the torque transmitted by the liquid crystal to an underlying surface. Other dopants, such as salts, permit manipulation of the electrical double layers that form at the interfaces of the liquid crystals and thus permit manipulation of the strength of anchoring of the liquid crystal at the interface. A number of methods for preparing interfaces between liquid crystals and aqueous phases lie within the scope of the present invention. An approximately planar interface can be prepared by a film of liquid crystal in contact with an aqueous phase, or alternatively a curved interface can be prepared by using a droplet of liquid crystal dispersed in an aqueous phase. The scope of the invention is not limited by the methods by which interfaces between aqueous phases and liquid crystals can be prepared by those skilled in the art.

Certain devices according to the invention further include an enhancing agent present in the aqueous phase that enhances the change in orientation of the liquid crystal upon interaction of the bioagent and target. Enhancing agents useful in this regard include, but are not limited to, L-α-dilauroyl phophatidylcholine (L-DLPC), phospholipids (such as DPPC, DMPC), glycolipids, saturated and unsaturated lipids, fatty acids, polymers that cause homeotropic anchoring, anionic surfactants, cationic surfactants, non-ionic surfactants, zwitterionic surfactants, amphiphilic molecules that generate known orientations of liquid crystals. In general, enhancing agents that generate known orientations of liquid crystal at the aqueous-liquid crystal interface are useful for this purpose.

In another aspect of the invention, a method for preparing a liquid crystal device for detecting the presence of a bioagent in a sample is provided. Such methods include steps of: (a) dissolving a cross-linking agent into a liquid crystal, and (b) adding a target of a bioagent to an aqueous phase that contacts said liquid crystal to cause an interfacial reaction between the target and the cross-linking agent. The interaction provides a membrane containing a polymerized target at the interface of the liquid crystal, the polymerized target positioned to interact with a bioagent contacted with the membrane. Subsequent interaction between bioagent and target causes an orientation change in the liquid crystal thereby indicating the presence of the bioagent. As described above, the membrane may further comprise non-target molecules including, but not limited to, self-assembled monolayers (SAMs) with which target molecules are cross-linked.

In yet another aspect of the invention, methods for detecting the presence of a bioagent in a sample are provided. Such methods include steps of: (a) forming a membrane containing a polymerized target for an enzyme at an interface between a liquid crystal and an aqueous phase; and (b) introducing a bioagent into the aqueous phase wherein interaction of the bioagent and polymerized target leads to a change in the orientational order of the liquid crystal. The orientational change indicates the presence of the bioagent in the sample.

In certain embodiments, the bioagent is an enzyme and the target is a substrate for the bioagent. Preferred embodiments are directed to the detection of neurotoxins with metalloprotease activities. Accordingly, the substrate is a peptide cleavable by said neurotoxin. For example, certain methods detect the presence of botulinum toxin using as substrate a peptide cleavable by botulinum toxin (e.g., SNAP-25 or a cleavable fragment thereof). The 206 amino acid sequence for human SNAP-25 (SEQ ID NO:1) is publicly available via the National Center for Biotechnology Information (NCBI) under accession no. P60880. The amino acid sequence for human SNAP-25 and related information provided at accession no. P60880 as of this application's filing date are incorporated herein by reference in their entirety. In other embodiments, the enzyme detected is a neurotoxin with phospholipase $A_2$ activity and the substrate is a 1,2-diacyl-3-sn-phosphoglyceride containing an sn-2 ester bond. A wide variety of such enzymes, namely neurotoxins, are known in the art and the present invention is particularly advantageous for use in their detection. An extensive list of neurotoxins are described in Schiavo et al., "Neurotoxins affecting Neuroexocytosis," *Physiological Reviews* 80:717-766 (2000), incorporated herein by reference.

In yet other embodiments, the devices and methods include a membrane that incorporates a target molecule that is a binding group for binding a protein of interest to the membrane. Accordingly, the invention provides in specific embodiments devices and methods for detecting the presence of an antibody in a sample by using an antigen recognized by the respective antibody. Alternatively, the invention provides specific embodiments in which the presence of an antigen in a sample is detected by forming a membrane containing an antibody. In these preferred embodiments, the membrane containing the antibody (for antigen detection) or antigen (for antibody detection) is prepared using substantially the same strategy as described above. In one preferred embodiment, the cross-linked membrane containing a protein or peptide antigen (for antibody detection) is prepared by adding adipoylchloride to the liquid crystal and the antigen to the aqueous phase. The reaction between the antigen and adipoylchloride at the interface between the aqueous phase and liquid crystal leads to the formation of a polymerized membrane containing antigen. To detect the presence of antibody in a sample, the sample containing antibody is added to the aqueous phase in contact with the polymerized membrane containing antigen. The binding of the antibody to the antigen containing membrane is detected by a change in order of the liquid crystal in contact with the membrane.

In preferred embodiment, enhancers are added to the aqueous phase to increase the change in order of the liquid crystal when the antibody is bound. Enhancing agents useful in this regard include, but are not limited to, L-α-dilauroyl phophatidylcholine (L-DLPC), phospholipids (such as DPPC, DMPC), glycolipids, saturated and unsaturated lipids, fatty acids, polymers that cause homeotropic anchoring, anionic surfactants, cationic surfactants, non-ionic surfactants, zwitterionic surfactants, amphiphilic molecules that generate known orientations of liquid crystals. In general, enhancing agents that generate known orientations of liquid crystal at the aqueous-liquid crystal interface are useful for this purpose. In other embodiments, the membrane is prepared as described above to contain the antibody; an antigen contained in a sample may then be detected via interaction between polymerized antibody and respective antigen.

As noted above, preferred embodiments of the invention are directed to a method that provides for the selective detection of an enzyme based on enzymatically cleavable peptide-containing membranes and liquid crystals. The membrane including the polymerized substrate for a specific enzyme or class of enzymes can be selectively degraded by contact with the enzyme. The degradation of the polymeric membrane fabricated at the interface between liquid crystals and aqueous phases changes the orientation of the liquid crystal in contact with the aqueous phase (FIGS. 1a and 1b). As a result, the presence of a protein can be recognized by monitoring the change in orientation of a liquid crystal using optical or electrical methods well known to those skilled in the art. In some embodiments of the invention, the change in ordering of the liquid crystal can be controlled by the addition of a phospholipid when exposed to aqueous phase (FIG. 1c). A merit of this detection method is that the presence of an enzyme can be monitored without a label attached to the analyte. The method also does not require a complicated surface patterning/functionalization procedure and special instrumentation. Therefore, in certain embodiments, the present invention offers efficient and cost-effective detection of biomolecules.

Figure 2:
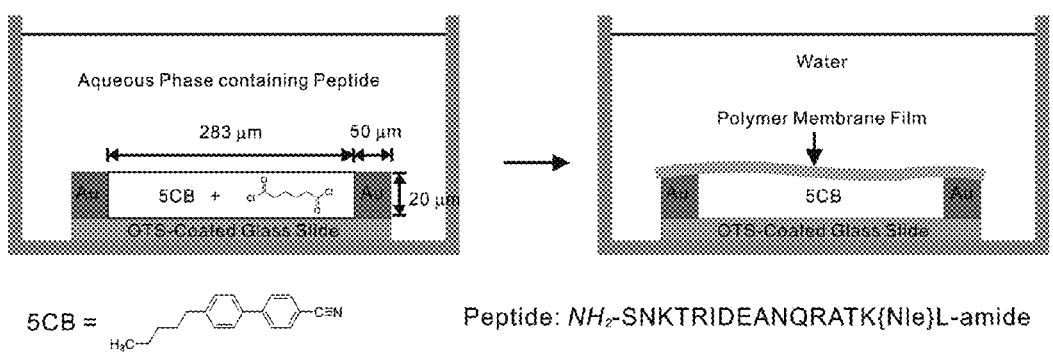
FIG. 2. Schematic representation of the polymerization of peptide at the aqueous-5CB interface and structures of 5CB and the peptide used in this experiment.

An illustrative example of a liquid crystal device, method of fabrication, and use according to the invention will now be described. In this example, an initial step is the preparation of a polymer membrane containing peptide substrates that can be recognized by an enzyme. FIG. 2 illustrates the polymerization of a peptide between thermotropic liquid crystals and aqueous phases. A natural peptide substrate was used in this example to show the possibility of practical applications of the invention. The 17-amino acid peptide shown in FIG. 2 (SEQ ID NO:3) contains residues 187-203 of SNAP-25, a 206-residue protein. The 17-mer peptide substrate is known to be effectively cleaved by botulinum neurotoxin type A (BoNT/A) metalloprotease, which is the most poisonous substance known. The methionine (M) at position 202 was replaced with the isosteric amino acid norleucine (Nle) to prevent oxidation of the peptide. The 17-amino acid peptide was synthesized and the crude peptide was purified by chromatography over a preparative scale C-18 column. The reverse-phase high performance liquid chromatography (HPLC) analyses confirmed the peptide had >98% purity, and MALDI-TOF mass spectrometry spectra confirmed its predicted mass.

The 17-amino acid peptide was polymerized with adipoyl chloride as a crosslinking agent at the interface between thermotropic liquid crystals and aqueous phases. The reaction of the peptide with adipoyl chloride leads to the formation of amide interpeptide linkages through lysines (K) in its sequence. It has been previously reported that a biodegradable polymer can be synthesized by the reaction of amino acids with adipoyl chloride. The adipoyl chloride was added to the liquid crystal 4-cyano-4'-pentylbiphenyl (5CB, shown in FIG. 2) and homogeneously mixed by using a vortex mixer. The composition of the mixture was prepared to be 1.3 wt. % adipoyl chloride in 5CB. The mixture was deposited into the pores of gold TEM grids supported on octyltrichlorosilane (OTS)-coated glass slides. Then, the peptide in aqueous NaOH solution (0.20 mM, pH 11.0) was introduced to the sample (FIG. 2). After being incubated for 2 hours at room temperature, the peptide solution was removed using a pipette and the sample was rinsed with water more than five times. In other embodiments of the invention droplets of liquid crystal containing cross-linking agent can be dispersed into an aqueous solution containing the substrate to be polymerized at the interface between the liquid crystal and aqueous phase.

Figure 3:
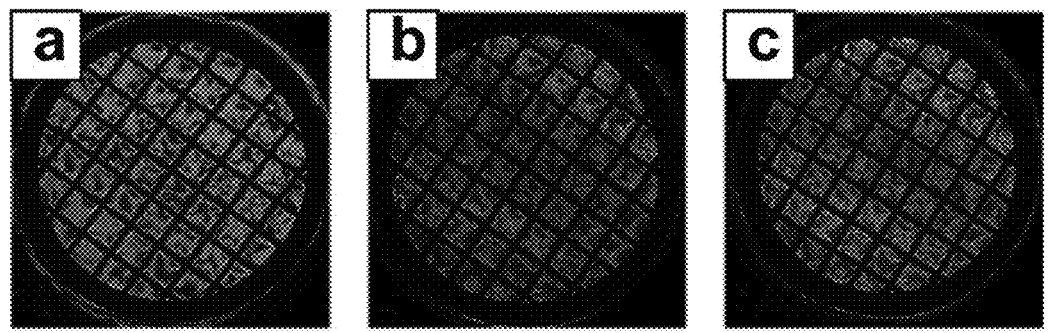
FIG. 3. Optical textures of 5CB mixed with adipoyl chloride (1.3 wt. %) after (a) 0 min and (b) 2 h contact with aqueous peptide solution (0.020 mM, pH 11.0), and then (c) 30 min after contact with a dispersion of vesicles of L-DLPC in water (0.1 mM, pH 8.0).

FIG. 3 shows the optical textures of 5CB monitored during polymerization. All optical textures reported herein were measured between crossed polarizers. The optical texture of 5CB doped with adipoyl chloride became bright immediately after contacting with the aqueous peptide solution (FIG. 3a). Since it is known that the OTS-coated glass slides cause homeotropic anchoring of 5CB on the surface, the orientation of 5CB at the aqueous-5CB interface is therefore near planar or planar. Under these circumstances, the tilt angle of 5CB relative to the surface normal is gradually decreases from ~0° at the OTS-treated glass to ~90° at the aqueous-5CB interface. When the tilt angle of the liquid crystal continuously varies across the film, nematic 5CB, because it possesses two direction-dependent refractive indices (is birefringent), can rotate the plane of polarization of the light, thus leading providing a bright optical appearance. FIG. 3b shows the optical image of 5CB doped with adipoyl chloride after 2 h of contact with the aqueous peptide solution at room temperature. The optical image became darker and darker during the formation of polymer at the aquesous-5CB interface.

To confirm the formation of polymerized peptide substrate, the aqueous peptide solution was removed using a pipette and a dispersion of vesicles of L-α-dilauroyl phosphatidylcholine (L-DLPC) in water (0.1 mM, pH 8.0) was subsequently introduced into the sample after washing with water several times and storing in water for 2 h at rt. In the absence of the polymer membrane, contact of an aqueous dispersion of L-DLPC with the interface of 5CB is known to cause the spontaneous transfer of the lipids onto the aqueous-5CB interface leading to a homeotropic alignment of 5CB at the interface. The homeotropic alignment can be confirmed by black optical appearance of 5CB between crossed polars and a conoscopic image. The inventors determined if the polymer membrane fabricated at the aqueous-5CB interface would block the transfer of phospholipids onto the interface and thus maintain the orientation of 5CB near planar or planar at the interface. After 30 min of immersion, the optical texture did not show the formation of black domains in the liquid crystal, confirming that the polymer membrane at the aqueous-5CB interface blocked the transfer of lipids onto the interface (FIG. 3c).

The enzyme trypsin was used to test the cleavage of polymer membrane. Trypsin is known to be selective in its cleavage of peptide bonds. Trypsin cleaves peptide bonds after (on the C-terminal side of) lysine (K) and arginine (R) if the next residue is not proline (P). The 17-mer peptide (FIG. 2) used in this example, therefore, contains four cleavage sites by trypsin after two lysine and two arginine residues in its sequence. To test the cleavage of polymer membrane at the aqueous-5CB interface, an aqueous trypsin solution (~21 μM, pH 8.0) was introduced into an aqueous solution in contact with the polymerized membrane. The pH of the trypsin solution was adjusted to 8 by a dilute aqueous NaOH solution to maximize the reactivity of trypsin. After being incubated for 2 hours at room temperature, the trypsin solution was removed by a pipette and the sample was rinsed with slightly basic water (pH 8) several times. To confirm the degradation of the polymer membrane by trypsin, an aqueous solution containing a dispersion of vesicles of L-DLPC (0.10 mM, pH 8.0) was introduced into the sample. It was anticipated that the degradation of the polymer membrane by trypsin would allow the transfer of phopholipids onto the aqueous-5CB interface (FIG. 1c), thus leading to an orientational transition in the liquid crystal that could be monitored optically.

Figure 4:
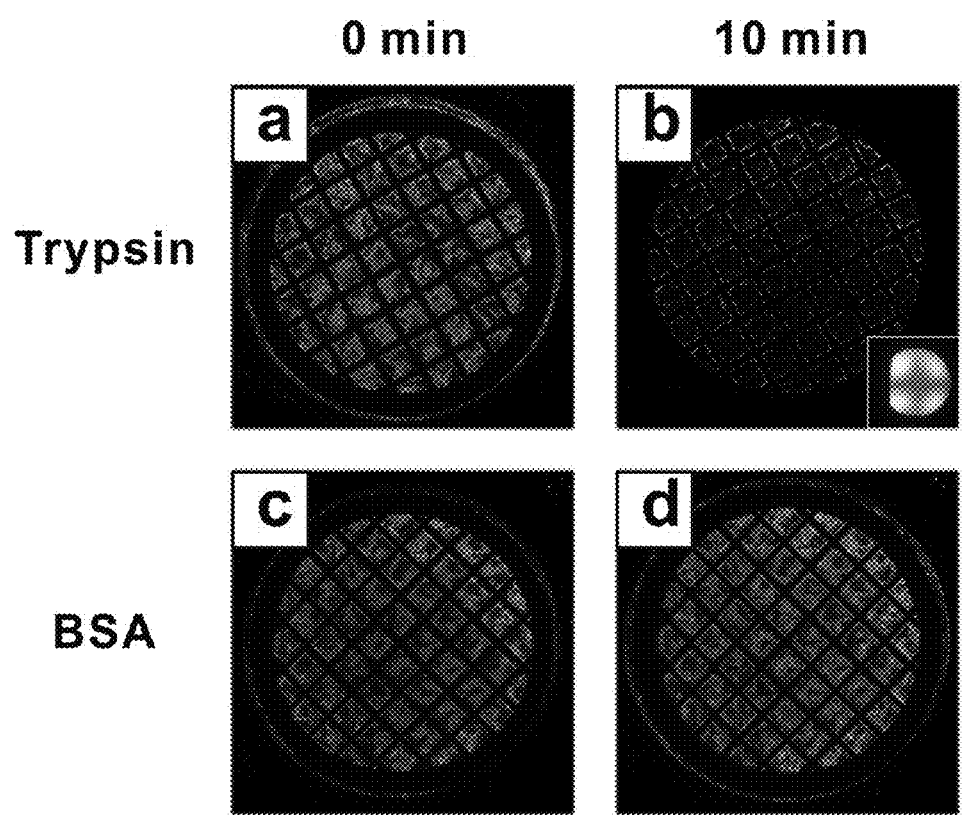
FIG. 4. Optical textures of 5CB fabricated with polymer membrane after (a) 0 min and (b) 10 min contact with a dispersion of vesicles of L-DLPC (0.1 mM) in water (pH 8.0). The sample in (a) and (b) was incubated in aqueous trypsin solution (21 μM, pH 8.0) for 2 h at rt before the addition of L-DLPC; Optical textures of 5CB fabricated with polymer membrane after (a) 0 min and (b) 10 min contact with a dispersion of vesicles of L-DLPC (0.1 mM) in water (pH 8.0). The sample in (c) and (d) was incubated in aqueous BSA solution (21 μM, pH 8.0) for 2 h at rt before the addition of L-DLPC.

The initial bright optical appearance of 5CB between crossed polars indicates that the orientation of 5CB is near planar at the aqueous-5CB interface (FIG. 4a). In contrast, after 10 min of contact with an aqueous dispersion of vesicles of L-DLPC (0.10 mM, pH 8.0), the optical texture of 5CB became black (FIG. 4b). The black appearance corresponds to liquid crystal anchored perpendicular to both the aqueous-5CB and the 5CB-OTS interfaces (FIG. 1c). In the case that the orientation of 5CB is perpendicular to both interfaces, the liquid crystal does not rotate the polarization plane of light leading to its dark appearance between crossed polars. The homeotropic anchoring was also confirmed by the conoscopic image (black cross in the inset of FIG. 4b).

To confirm that the orientational transition arises from the degradation of polymer membrane by the enzyme trypsin, a protein was tested which can not hydrolyze the polymer membrane. Instead of the trypsin solution, an aqueous solution of bovine serum albumin (BSA) (21 μM, pH 8.0) was incubated against the polymerized peptide membrane fabricated at the aqueous-5CB interface.

After being incubated for 2 h at room temperature, the BSA solution was removed and the sample was rinsed with deionized water more than five times. Then, like the previous experiment with trypsin, an aqueous dispersion of vesicles of L-DLPC (0.10 mM, pH 8.0) was introduced into the sample. In contrast to the results obtained with trypsin, the optical appearance of 5CB remained bright even after 10 min contact with the L-DLPC dispersion (FIGS. 4c and 4d). The homeotropic anchoring of 5CB was not observed even after 1 h of contact with L-DLPC. The results demonstrate that the orientational transition of 5CB observed with the sample treated with trypsin (FIGS. 4a and 4b) arises from the selective cleavage of the polymer membrane by trypsin. The method presented here, therefore, can be used to differentiate proteins that can/cannot cleave polymer membrane when an appropriate peptide substrate is employed.

Figure 5:
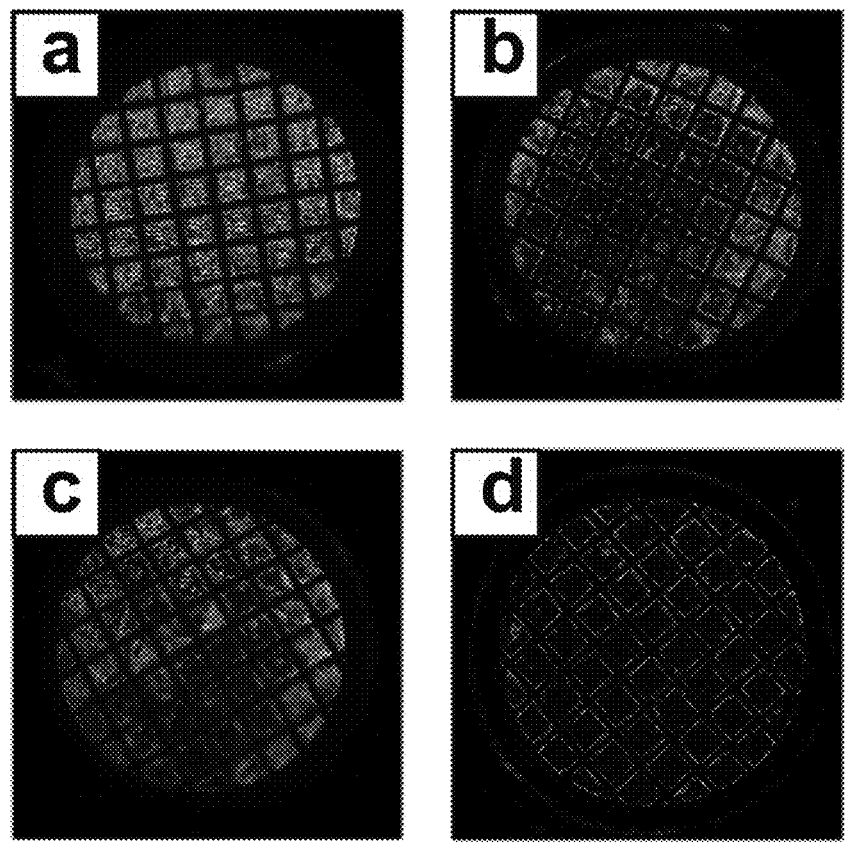
FIG. 5. Optical images (transmission through crossed polars) of liquid crystals in contact with polymerized membrane after incubation in (a) 2 nM, (b) 20 nM, (c) 0.2 μM, and (d) 21 μM trypsin in water (pH 8) for 2 h, and then after 30 min of contact with 0.1 mM L-DLPC in water (pH 8).

Aqueous trypsin solutions of various concentrations ranging from 2 nM to 21 μM (pH 8.0) were prepared and tested using a polymer membrane prepared as described above. After 30 min of immersion in aqueous dispersions of vesicles of L-DLPC (0.10 mM, pH 8.0), the sample incubated in 2 nM trypsin solution showed small black domains (FIG. 5a). In contrast, the samples incubated in trypsin solutions of higher concentrations (20 nM, 0.2 μM, and 21 μM) exhibited transition from planar to homeotropic anchoring in most areas (FIGS. 5b, 5c, and 5d) indicating degradation of polymer membrane by trypsin. These results demonstrate detection of trypsin at concentrations near 2 nM under the above described conditions. It is anticipated that the detection limit can be lowered by optimizing experimental conditions such as the thickness of polymer membrane and temperature. The thickness of polymer film can be decreased by decreasing the concentrations of adipoyl chloride in 5CB and peptide in water.

Figure 11:
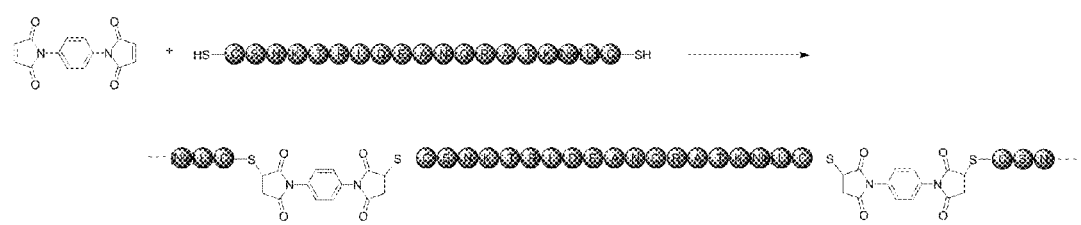
FIG. 11. Schematic illustrate of the use of dimaleimide cross-linkers and HS-containing peptides to prepare a polymerized peptide membrane.

A convenient method for detection of an enzyme using an enzymatically cleavable protein-containing membrane at the interface between liquid crystal and aqueous phases is demonstrated herein. The method can be used to monitor the presence of a variety of enzymes when an appropriate peptide substrate for a specific enzyme is incorporated. It should be noted that the 17-amino acid peptide used in the foregoing example is the substrate that is effectively cleaved by botulinum neurotoxin type A (BoNT/A) which is an extremely lethal substance. Thus, the method disclosed herein can be directly applied to detect the BoNT/A without any major modification. Fast detection of BoNT/A is important for public health and food safety. The above example using an oligomeric peptide substrate is illustrative, and the method can also be applied to the preparation of peptide substrates that are polymers, including proteins. As well, the method is not limited to the use of adipoylchloride as the cross linker— many cross-linking agents for peptides, proteins, nucleic acids are known to those skilled in the art. Various cross-linking agents containing two maleimide groups and peptides or proteins containing—SH groups are shown in FIG. 11.

Accordingly, it is contemplated that the polymeric material used to fabricate the polymerized substrates incorporate peptide sequences that serve as recognition elements for the analyte/bioagent to be detected. It is noted that the peptide sequences can serve as recognition elements for other types of agents, such as chemical agents, without deviating from the scope of the present invention. The peptide sequences provide a molecular basis for sensor specificity, as well as, the mechanism by which the polymerized substrate erodes (i.e., peptide bond cleavage) when exposed to the predetermined bioagent. It can be appreciated that a polymerized substrate acting as biological sensor possesses several advantages within a microfluidic platform. For example, small amounts of reagents are needed to produce these polymerized substrates. Further, these substrates are thin, lowering the diffusion path length of the agent to be detected (i.e. large enzymes, toxins and proteases).

In yet other embodiments, the method detects the presence of an antibody in a sample by using an antigen recognized by the respective antibody. The invention provides specific embodiments in which the presence of an antigen in a sample is detected by forming a membrane containing an antibody. In these preferred embodiments, the membrane containing the antibody (for antigen detection) or antigen (for antibody detection) is prepared using strategies substantially similar to those described above. In one preferred embodiment, the cross-linked membrane containing a protein or peptide antigen (for antibody detection) is prepared by adding adipoyl-chloride to the liquid crystal and the antigen to the aqueous phase. The reaction between the antigen and adipoylchloride at the interface between the aqueous phase and liquid crystal leads to the formation of a polymerized membrane containing antigen. To detect the presence of antibody in a sample, the sample containing antibody is added to the aqueous phase in contact with the polymerized membrane containing antigen. The binding of the antibody to the antigen containing membrane is detected by a change in order of the liquid crystal in contact with the membrane.

In preferred embodiment, enhancers are added to the aqueous phase to increase the change in order of the liquid crystal when the antibody is bound. Enhancing agents useful in this regard include, but are not limited to, L-α-dilauroyl phophatidylcholine (L-DLPC), phospholipids (such as DPPC, DMPC), glycolipids, saturated and unsaturated lipids, fatty acids, polymers that cause homeotropic anchoring, anionic surfactants, cationic surfactants, non-ionic surfactants, zwitterionic surfactants, amphiphilic molecules that generate known orientations of liquid crystals. In general, enhancing agents that generate known orientations of liquid crystal at the aqueous-liquid crystal interface are useful for this purpose. In other embodiments, the membrane is prepared as described above to contain the antibody; an antigen contained in a sample may then be detected via interaction between polymerized antibody and respective antigen.

The following examples are offered for further illustrative purposes related to the above-described devices and methods, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Preparation of a device containing a polymerized membrane at the interface between a nematic liquid crystal and an aqueous phase—the polymerized membrane containing the peptide substrate for botulinum toxin.

This example describes the polymerization of peptides with adipoyl chloride at interfaces between thermotropic liquid crystals and aqueous phases. The sequences of peptides used in this example are shown below. The HPLC analyses confirmed the peptides had >98% purity, and MALDI-MS spectra confirmed their structures.

Peptide I: $NH_2$-CSNKTRIDEANQRATK{Nle}LC-amide (SEQ ID NO:2)

Peptide II: $NH_2$-SNKTRIDEANQRATK{Nle}L-amide (SEQ ID NO:3)

Figure 6:
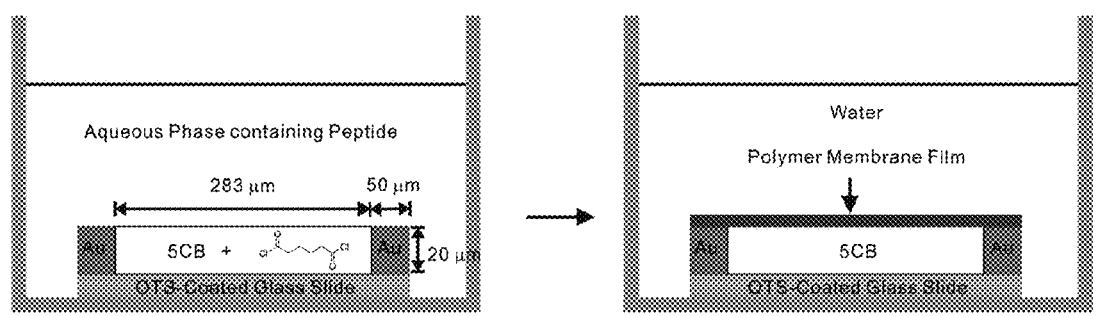
FIG. 6. Fabrication of enzymatically degradable polymer membrane at interface between liquid crystal and aqueous phase.

These peptides were polymerized with adipoyl chloride as a cross linker at the interface between liquid crystals and aqueous phases. The adipoyl chloride was added to the liquid crystal 4-cyano-4'-pentylbiphenyl (5CB) and homogeneously mixed by sonication. The composition of the mixture was about 1.5 wt. % adipoyl chloride in 5CB. The mixture was deposited into the pores of gold TEM grids supported on octyltrichlorosilane (OTS)-coated glass slides. The peptide in aqueous NaOH solution (0.20 mM, pH 11) was introduced to the sample (FIG. 6). After polymerization for 2 hours at room temperature, the peptide solution was removed and the sample was rinsed with a slightly basic water (pH 8) more than five times.

Example 2

Degradation of a substrate containing polymerized membrane using trypsin

Figure 7:
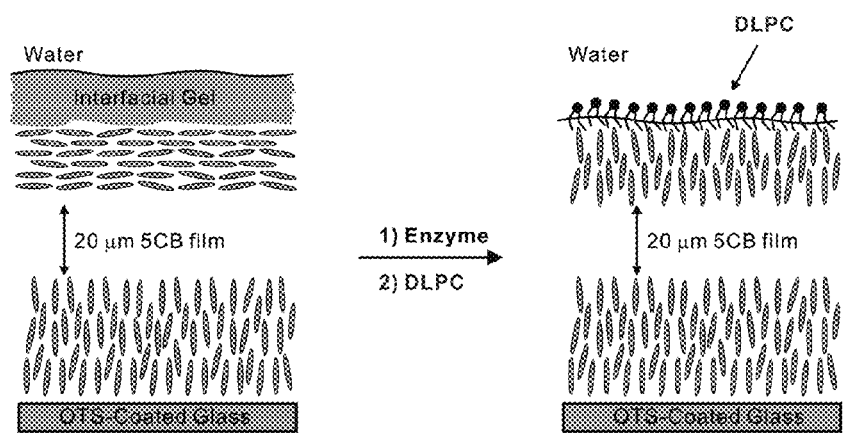
FIG. 7. Degradation of polymer membrane and the subsequent assembly of phospholipids at the interface between liquid crystals and aqueous phases.

In this example, trypsin was selected as a model enzyme to test the cleavage of a polymer membrane. Trypsin is known to be selective in its cleavage of peptide bonds. Trypsin only cleaves the peptide bonds after (on the C-terminal side of) lysine (K) and arginine (R) if the next residue is not proline (P). Therefore, the peptide I and II contain four cleavage sites by trypsin after two lysine and two arginine residues in its sequence. An aqueous trypsin solution (~21 μM, pH 8) was introduced into the sample. After being incubated for 2 hours at room temperature, the trypsin solution was removed and the sample was rinsed with slightly basic water (pH 8) several times. To confirm the degradation of the polymer membrane by trypsin, an aqueous solution containing a dispersion of vesicles of L-α-dilauroyl phophatidylcholine (L-DLPC) was introduced into the sample. The degradation of the polymer membrane allows the assembly of phopholipids at the interface between liquid crystals and aqueous phases (FIG. 7). As a result, the degradation of the polymer membrane can be confirmed by monitoring orientational transitions in liquid crystals triggered by the spontaneous assembly of the phospholipid.

Figure 8:
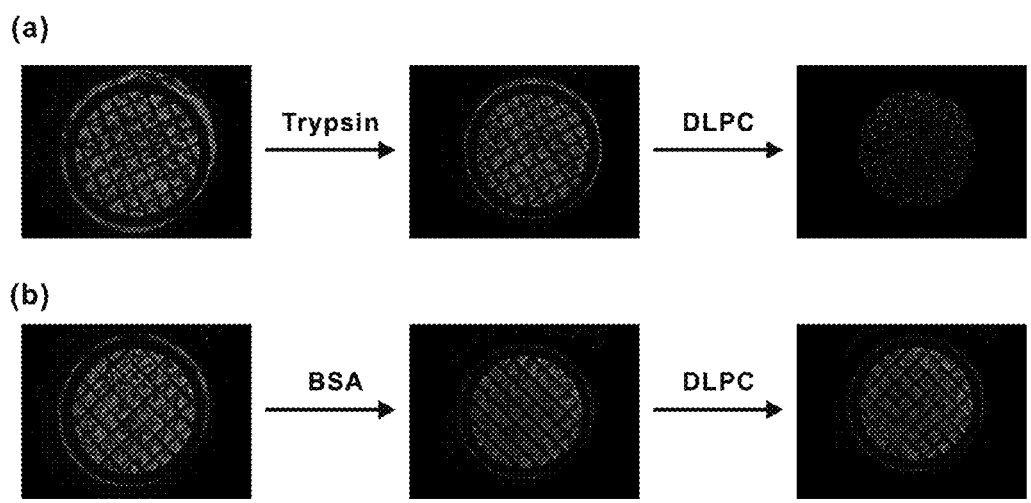
FIG. 8. Optical images (transmission through crossed polars) of liquid crystals after incubated in (a) 21 μM trypsin or (b) 21 μM BSA in water (pH 8) for 2 h, and then in 0.1 mM L-DLPC in water (pH 8).
Figure 9:
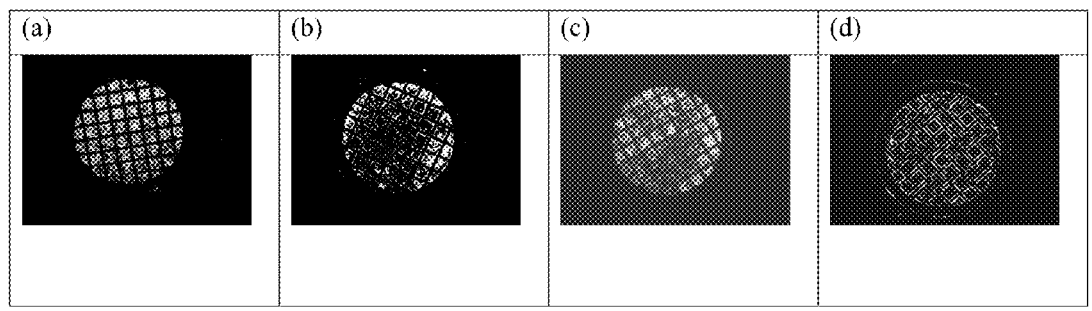
FIG. 9. Optical images (transmission through crossed polars) of liquid crystals after incubation in (a) 2 nM, (b) 20 nM, (c) 0.2 μM, and (d) 21 μM trypsin in water (pH 8) for 2 h, and then 0.1 mM L-DLPC in water (pH 8).

Within 10 min of immersion in an aqueous solution containing a dispersion of vesicles of L-DLPC, the optical texture viewed between crossed polars became black (FIG. 8a). The black domains correspond to liquid crystal that is anchored perpendicular to both the liquid crystal-water and the liquid crystal-OTS interfaces (FIG. 7). As a control, a protein which can not cleave the polymer membrane was also tested. An aqueous solution of bovine serum albumin (BSA) (21 μM, pH 8) was introduced into the polymer sample instead of the trypsin solution. After reacting for 2 hours at room temperature, the BSA solution was removed and the sample was rinsed with slightly basic water more than five times. Even after an aqueous solution containing a dispersion of vesicles of L-DLPC was introduced into the sample, the liquid crystal remained bright (FIG. 8a-b). These results, as a whole, show that the method allows differentiation of proteins that can/ cannot cleave the polymer membranes by using liquid crystals.

The inventors investigated aqueous trypsin solutions of various concentrations ranging from 2 nM to 21 µM (pH 8) for degradation of the polymer membrane. After the introduction of L-DLPC, all samples showed regions of homeotropic alignment indicating the activity of the enzyme. The highest concentrations caused the liquid crystal to appear almost completely black between crossed polars (FIG. 9a-d).

Example 3

Detection of the light chain of botulinum toxin

Figure 10:
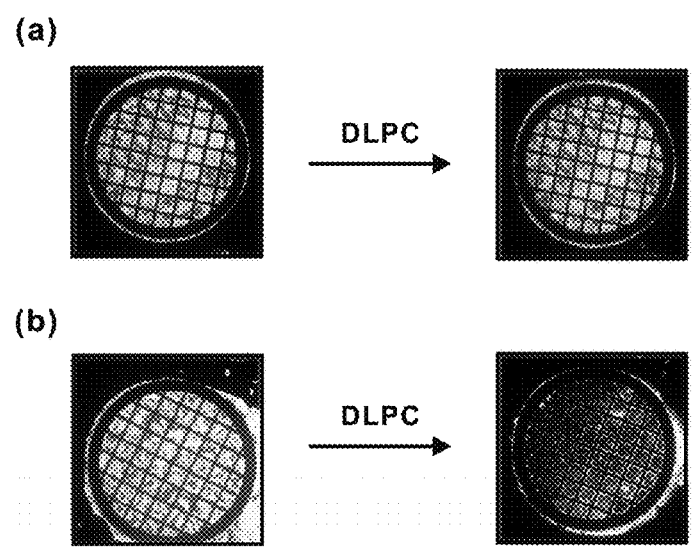
FIG. 10. Optical images (transmission through crossed polars) of liquid crystals in contact with polymerized membrane of substrate for BoNT/A after incubation in (a) water (pH 8) or (b) 50 nM BoNT/A light chain in water (pH 8) for 24 h, and then in 0.1 mM L-DLPC in water (pH 8).

The peptides used in this example (Peptide I and II) contain residues 187-203 of SNAP-25. The peptides are known to be effectively cleaved by botulinum neurotoxin type A (BoNT/ A), the most lethal substance known. Therefore, the system used for trypsin can be applied to detect BoNT/A without major modification. The procedure for polymerization was same as described above (see Example 1). After polymerization, water (pH 8) or an aqueous solution of BoNT/A light chain (pH 8) was introduced to the sample. After incubated for 24 hours at room temperature, the solutions were removed and the sample was rinsed with water more than 5 times. When a dispersion of vesicles of L-DLPC was introduced to the sample, only the sample incubated in aqueous BoNT/A light chain solution exhibited the transition of 5CB anchoring from planar to homeotropic at the aqueous-5CB interface (FIG. 10a-b). The results indicates that the polymer membrane is cleaved by BoNT/A light chain, and thus the system can be used to detect the presence of BoNT/A. This system provides a novel method for the detection of various biomolecules when an appropriate peptide substrate is incorporated.

Example 4

Formation of a polymerized peptide membrane using maleimide cross-linkers.

The inventors synthesized the 19-amino acid peptide (SEQ ID NO:2), which contains residues 187-203 of SNAP-25 and two cysteines at both ends. The sulfhydryl groups of terminal cysteines provide the opportunity to conjugate the synthetic peptide to the maleimide containing crosslinker (FIG. 11).

The 1,4-dimaleimidobenzene (0.0035 g) was mixed with the liquid crystal 4-cyano-4'-pentylbiphenyl (5CB, 0.2076 g) by using a vortex mixer. The mixture was deposited into the pores of gold TEM grids supported on octyltrichlorosilane (OTS)-coated glass slides. The 0.20 mM solution of the 19-amino acid peptide in phosphate buffer (aqueous 20 mM; pH 7.0) was prepared and introduced to the sample. After being incubated for 3 h at room temperature, the peptide solution was removed using a pipette and the sample was rinsed with water several times. The sample was stored in an oven held at 36° C. for 2 h.

Figure 12:
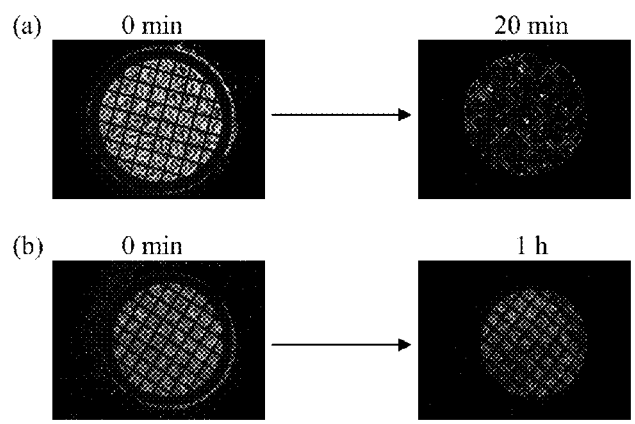
FIG. 12 Optical images (crossed polars) of (a) pure 5CB and (b) 5CB in contact with a polymer membrane fabricated according to the chemistry shown in FIG. 1, after 0 min and 1 h contact with the vesicle dispersion of L-DLPC in water (0.1 mM; pH 8.0).

To confirm the formation of polymer at the aqueous-5CB interface, a dispersion of vesicles of L-a-dilauroyl phosphatidylcholine (L-DLPC) in water (0.1 mM; pH 8.0) was introduced to the sample. In the absence of the polymerized membrane contact of a vesicle dispersion of L-DLPC with 5CB leads to a homeotropic alignment of 5CB at the interface within about 20 min (FIG. 12a). In contrast, after even 1 h of immersion, the optical texture of 5CB with the polymer membrane showed only small areas of homeotropic alignment of 5CB indicating the formation of a polymer membrane at the interface by using a dimaleimide-based cross-linker (FIG. 12b).

Accordingly, various aspects of the present have been shown including: (a) the formation of devices that include a polymerized membrane between a liquid crystal and an aqueous phase, including an example in which the membrane contains a substrate for an enzyme; (b) the practice of methods wherein the addition of a cross linking agent to the liquid crystal and a substrate for an enzyme to the aqueous phase leads to the formation of a polymerized membrane containing the substrate at the interface between the liquid crystal and the aqueous phase; and (c) the performance of methods wherein a polymerized membrane containing a substrate to trypin and botulinum toxin prepared at the interface between the liquid crystal and aqueous phase is used to report the presence of trypsin and the light chain of botulinum toxin.

Example 5

Amplification of enzymatic activities using oligopeptides cross-linked at interfaces between aqueous phases and liquid crystals In this example, a strategy for cross-linking of oligopeptides at aqueous-liquid crystal interfaces is provided. This example also describes the response of liquid crystals to the cross linking of oligopeptides and the cleavage of the oligopeptides by an enzyme. To test the strategy, the inventors used a 17-amino acid oligopeptide (FIG. 13; SEQ ID NO:3) that is the substrate of botulinum neurotoxin type A (BoNT/ A) because the ultimate goal of this example is the detection of BoNT/A by using this oligopeptide-modified interface. In view of the dangers associated with botulinum toxing, the inventors used trypsin as a model enzyme that also can cleave the 17-amino acid oligopeptide.

Figure 13:
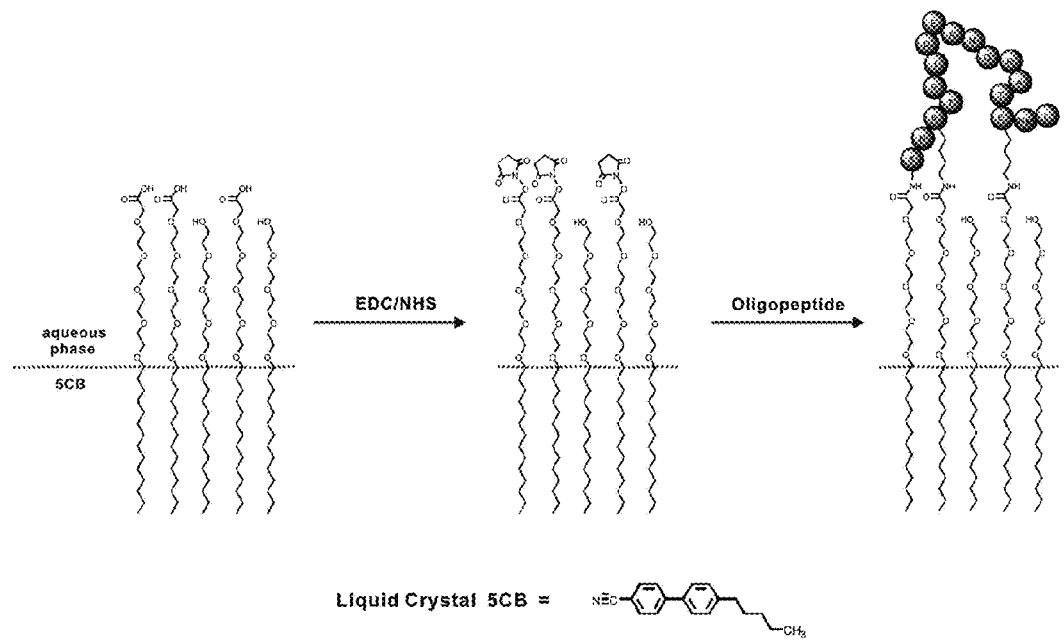
FIG. 13. Immobilization of a 17-amino acid oligopeptide at a mixed monolayer presenting carboxylic acid groups and tetra(ethylene glycol) groups through activation of the carboxylic acid groups by EDC/NHS.

This example is organized into three parts. First, the preparation of a mixed monolayer of OH— and $CO_2$H-terminated surfactants at aqueous-liquid crystal interfaces and the immobilization of the oligopeptide at the mixed monolayer through the N-hydroxylsuccinimide (NHS)-activation of carboxylic acid groups in the monolayer is described (FIG. 13). Second, the orientational response of liquid crystals to the immobilization of the oligopeptide is described and a possible mechanism for the anchoring transition is proposed. Finally, the oligopeptide-modified interface is used to detect an enzymatic activity and demonstrate the selectivity of this detection system.

Experimental Section

Materials. The 17-amino acid oligopeptide was synthesized at the Biotechnology Center at the University of Wisconsin-Madison using a Fmoc protocol with an Applied Biosystems Synergy 432A instrument. A detailed procedure of the synthesis has been previously reported. All aqueous solutions were prepared using deionized water. Deionization of a distilled water source was performed using a Milli-Q system (Millipore, Bedford, Mass.) to give water with a resistivity of 18.2 MΩ cm. The liquid crystal 4-cyano-4'-pentylbiphenyl (5CB) was purchased from EM Industries (Hawthorne, N.Y.). Tetraethylene glycol monotetradecyl ether (C14EG4), N-hydroxylsuccinimide (NHS), ethanolamine, octyltrichlorosilane (OTS), trypsin, trypsin-chymotrypsin inhibitor from *Glycine max* (Bowman-Birk inhibitor), DL-lysine, and poly-L-lysine hydrobromide (M.W. 1,000-4,000) were purchased from Aldrich (Milwaukee, Wis.). 1-Ethyl-2-[3-dimethylaminopropyl]carbodiimide hydrochloride (EDC) was purchased from Pierce Biotechnology (Rockford, Ill.). 3,6,9,12,15-Pentaoxanonacosanoic acid (C14EG4-CO$_2$H) was purchased from LaboTest (Niederschöna, Germany), and bovine serum albumin (BSA) was purchased from Jackson ImmunoResearch Laboratories (West Grove, Pa.). (2-(2-(2-(2-(2-(2-(2-(11-mercaptoundecyloxy)ethoxy)ethoxy)ethoxy)ethoxy)ethoxy)acetic acid was purchased from Prochimia (Gdansk, Poland). The glass microscope slides and eight-well chamber slides were purchased from Fisher Scientific (Pittsburgh, Pa.). Gold electron microscopy grids (20 μm thickness, 50 μm bar width, and 283 μm hole width) were purchased from Electron Microscopy Sciences (Hatfield, Pa.).

Preparation of Self-Assembled Monolayers (SAMs) on Gold. Gold films used in the surface IR experiments were prepared on silicon wafers mounted on a rotating planetary in an electron beam evaporator (VES-3000-C, Tek-Vac Industries, Brentwood, N.Y.). The rotation of the substrates during deposition ensured that the gold films were deposited without a preferred direction of incidence. The silicon wafers were first coated with 100 Å of titanium at a rate of ~0.2 Å/s to promote the adhesion between the silicon wafers and gold. Gold (thickness ~2000 Å) was then deposited at a rate of ~0.2 Å/s. The substrates coated with gold films were cut into pieces (ca. 0.5×2.5 cm), rinsed with absolute ethanol, and then dried under a stream of nitrogen. The slides were immersed in 0.1 mM ethanolic solution of (2-(2-(2-(2-(2-(2-(2-(11-mercaptoundecyloxy)ethoxy)ethoxy)ethoxy)ethoxy)ethoxy)ethoxy)acetic acid for 24 h. The resulting self-assembled monolayers (SAMs) were thoroughly rinsed with ethanol and dried using a gaseous stream of nitrogen before use.

Preparation of Optical Cells. Glass microscope slides were cleaned and functionalized with OTS according to the previously reported procedures. The OTS-coated glass slides were cut into pieces (ca. 5 mm×5 mm) and the pieces were fixed on the bottom of each well of an eight-well chamber slide with epoxy. Gold electron microscopy grids were then placed onto the OTS-coated glass slides. The 5CB was dispensed onto the grids supported on the OTS-coated glass slides, and the excess liquid crystal was removed by using a capillary tube. Aqueous phosphate buffered saline (PBS) (10 mM phosphate, 120 mM NaCl, 2.7 mM KCl; pH 7.6) was quickly introduced into the well with a syringe. To prepare a mixed monolayer of surfactants at the aqueous-liquid crystal interface, the solution was prepared by probe sonication (at 8 W for 5 min) of a mixture of tetraethylene glycol monotetradecyl ether and 3,6,9,12,15-pentaoxanonacosanoic acid dissolved in the PBS (0.20 mM and 0.80 mM, respectively). The PBS contacting with liquid crystal was exchanged with the aqueous solution of surfactants. The aqueous solution was equilibrated with the interface of the liquid crystal for 1 h at rt. Throughout the experiment, aqueous solutions were always exchanged such that the meniscus did not fall below the liquid crystal interface to prevent the displacement of the liquid crystal from the grid.

Cross linking of Oligopeptides. The aqueous solution was exchanged five times with the PBS (pH 7.6) before any other aqueous solution was introduced into the well. The solution of NHS (0.017 g) and EDC (0.115 g) in 3.0 mL of the PBS was introduced into the well and equilibrated with the mixed monolayer for 1.5 h at rt. Then, the NHS/EDC solution was replaced with the solution of 17-amino acid oligopeptide in the PBS (0.20 mM). After 1.5 h at rt, the oligopeptide solution was replaced with the solution of ethanolamine in the PBS (20 mM) to quench remaining NHS-activated carboxylic acid groups. The ethanolamine solution was allowed to be reacted for 30 min at rt before the protein solution of interest is introduced. The solutions of trypsin, trypsin and trypsin inhibitor, and BSA were prepared in 30 mM HEPES buffer (pH 8.0) with 20 mM CaCl$_2$. Before the introduction of the protein solutions, the aqueous solution was exchanged five times with the HEPES buffer.

Characterization. The optical images of liquid crystals were monitored between crossed polarizers of an optical microscope (BX60, Olympus, Tokyo, Japan). The optical images were captured using a digital camera (Olympus C-4000 Zoom) with consistent settings of the microscope (50% of maximum intensity, 10% open aperture, 4× magnification) and camera (f-stop of 2.8 and shutter speed of $\frac{1}{320}$ s). IR measurements were performed using a Nicolet Magna-IR 860 Fourier transform spectrometer equipped with a liquid nitrogen cooled mercury-cadmium-telluride (MCT) detector, a photoelastic modulator (PEM-90, Hinds Instruments, Hillsboro, Oreg.), and a synchronous sampling demodulator (SSD-100, GWC Technologies, Madison, Wis.). The polarized light was reflected from the gold films at an angle of incidence of 83°.

Results and Discussion

Cross-linking of Oligopeptides to NHS-activated Carboxylic Acid Groups. Before describing the immobilization of oligopeptides at an aqueous-liquid crystal interface, the inventors first investigated the covalent coupling of primary amine groups of the oligopeptide to NHS-activated carboxylic groups on a solid surface. Past studies showed that EDC reacts with carboxylic acid groups to form O-acylisourea intermediate that readily reacts with a primary amine group but also undergoes fast hydrolysis. Therefore, the carboxylic acid groups are activated with EDC in the presence of NHS to form N-succinimidyl esters that also quickly react with a primary amine group. Our group has reported the coupling of lysine residues of a protein ribonuclease A (RNase A) to NHS-activated carboxylic acid groups on a mixed self-assembled monolayer (SAM). Luk and coworkers have previously-described the covalent coupling of RNase A containing 10 lysine residues and a primary amine group at the N-terminal with a NHS-activated surface and their binding ability by using ellipsometry and the orientational behavior of liquid crystals. Here, the inventors investigated the covalent coupling of the 17-amino acid oligopeptide that will be used for our further experiments with a NHS-activated surface by polarization modulation infrared reflection-absorption spectroscopy (PM-IRRAS). The 17-amino acid oligopeptide possess two lysine residues and a primary amine group at the N-terminal, and thus could form covalent bonds to NHS-activated carboxylic acid groups immobilized on a surface.

Figure 14:
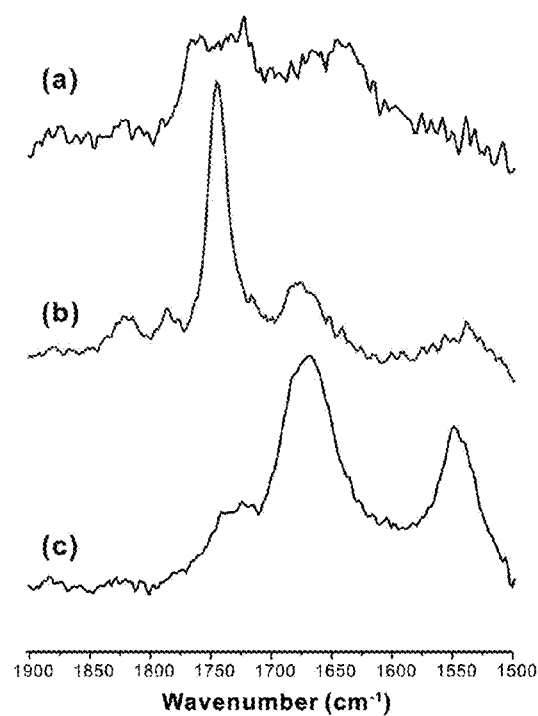
FIG. 14. PM-IRRAS spectra of a SAM derived from EG6-$CO_2H$ thiol on gold (a) before and (b) after 1.5 h of reaction with EDC/NHS, and then (c) after 1.5 h of reaction with 17-amino acid oligopeptide.

In order to investigate the coupling by PM-IRRAS, the inventors prepared the CO$_2$H-terminated surface by self-assembly of (2-(2-(2-(2-(2-(2-(2-(11-mercaptoundecyloxy)ethoxy)ethoxy)ethoxy)ethoxy)ethoxy)ethoxy)acetic acid on gold. FIG. 14a shows the PM-IRRAS spectrum of the CO$_2$H-terminated SAM in the carbonyl stretching region. The inventors assigned the peak at ~1745 cm$^{-1}$ to the carbonyl stretch of the free carboxylic acid groups and hydrogen-bonded carboxylic groups on the surface. The inventors then immersed the CO$_2$H-terminated SAM in NHS/EDC solution (50 mM/200 mM) in phosphate buffered saline (PBS) (10 mM phosphate, 120 mM NaCl, 2.7 mM KCl; pH 7.6) for 1 h at rt. The SAM was thoroughly washed with deionized water and ethanol, and dried under a stream of nitrogen before PM-IRRAS measurements. FIG. 14b shows the PM-IRRAS spectrum of the NHS-activated surface. The inventors observed the appearance of three new bands at 1745, 1785, and 1821 cm$^{-1}$. Based on the past study by Frey and Corn, the inventors assigned the peaks at 1745 and 1785 cm$^{-1}$ to asymmetric and symmetric stretch of the NHS carbonyls, respectively. They also assigned the peak at 1821 cm$^{-1}$ to the carbonyl stretch of the NHS ester. To test the coupling of the 17-amino acid oligopeptide with the NHS-activated surface, we immersed the NHS-activated SAM in a 0.20 mM aqueous 17-amino acid oligopeptide solution in the PBS for 1 h at rt, and measure the PM-IRRAS spectrum of the surface. As shown in FIG. 14c, the peaks corresponding to the NHS carbonyls and NHS ester disappeared and three new bands at 1549, 1668, and 1724 cm$^{-1}$ appeared. The inventors assigned the peak at 1549 cm$^{-1}$ to the NH bend of an amide, the peak at 1668 cm$^{-1}$ to the amide carbonyl stretch, and the peak at 1549 cm$^{-1}$ to the carbonyl stretch of remaining carboxylic acid groups or carboxylic acid groups in the 17-amino acid oligopeptide. It was noted that the 17-amino acid oligopeptide contains many amide bonds and the PM-IRRAS spectra cannot distinguish those amide bonds from the amide bonds formed from NHS-activated carboxylic acid groups. Nevertheless, the disappearance of the peaks corresponding to the NHS groups suggests that the treatment of the NHS-activated surface with the 17-amino acid oligopeptide leads to the conversion of NHS-activated carboxylic groups to amides. It can therefore be concluded that the 17-amino acid oligopeptide forms covalent bonds with the NHS-activated carboxylic acid groups at an interface.

Figure 15:
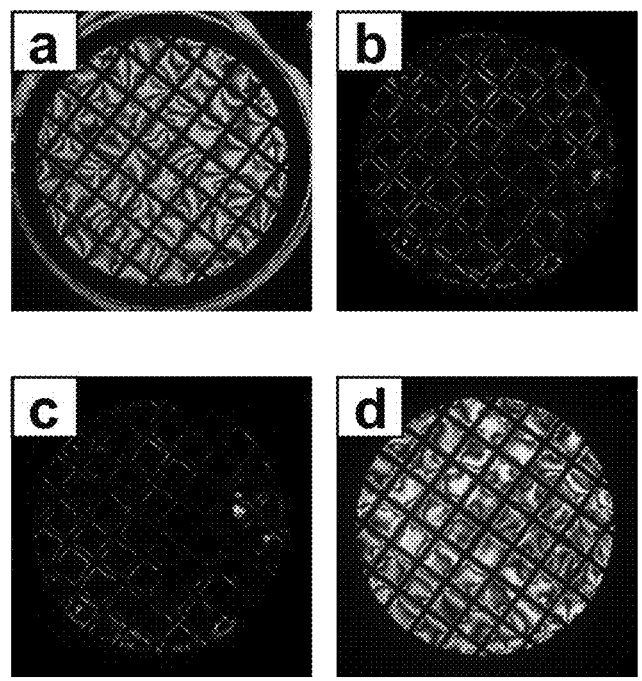
FIG. 15. Polarized light micrographs of 5CB (crossed polars) (a) in contact with PBS buffer (pH 7.6), (b) after 1 h of contact with an aqueous mixture of carboxyl-/hydroxyl-terminated surfactants (0.80/0.20 mM; PBS buffer, pH 7.6), (c) after 1.5 h of reaction with EDC/NHS (50/200 mM; PBS buffer, pH 7.6), and then (d) after 1.5 h of contact with an aqueous solution of 17-amino acid oligopeptide (0.020 mM; PBS buffer, pH 7.6).

Orientational Response of Liquid Crystal to Oligopeptide Cross-linking. The inventors investigated the orientational responses of liquid crystals during immobilization of the oligopeptide at an aqueous-liquid crystal interface. All optical images of liquid crystals presented in this example were obtained between crossed polarizers of an optical microscope. Before immersion under an aqueous solution, the 5CB contacting with the OTS-coated glass slide and air appeared dark. Since the anchoring of the liquid crystal at the liquid crystal-OTS interface is homeotropic (perpendicular), the dark appearance indicates a perpendicular orientation of the liquid crystal at the air-liquid crystal interface. The inventors first introduced phosphate buffered saline (PBS) (10 mM phosphate, 120 mM NaCl, 2.7 mM KCl; pH 7.6) to the sample using a syringe. The optical appearance of 5CB became bright indicating the orientational transition of liquid crystals from perpendicular to planar or tilted alignment at the aqueous-liquid crystal interface (FIG. 15a). In order to prepare a mixed monolayer of OH— and CO$_2$H-terminated surfactants at the liquid crystal interface, we prepared an aqueous solution of 0.20 mM tetraethylene glycol monotetradecyl ether (C14EG4) and 0.80 mM 3,6,9,12,15-pentaoxanonacosanoic acid (C14EG4-CO$_2$H) in PBS (pH 7.6). After removal of the PBS contacting with the liquid crystal, the inventors added the aqueous solution of mixed surfactants to the sample. Within 1 min of contact with the surfactant solution, the optical appearance of 5CB became uniformly dark indicating the anchoring of 5CB perpendicular to both the aqueous-liquid crystal and liquid crystal-OTS interfaces (FIG. 15b), indicating the transfer of the surfactants onto the aqueous-liquid crystal interface. Next, the inventors exchanged the aqueous solution with NHS/EDC solution (50 mM/200 mM) in PBS (pH 7.6) in order to activate the carboxylic acid groups at the interface. During the NHS-activation for 1.5 h at rt, the optical appearance of 5CB remained dark indicating homeotropic alignment of 5CB (FIG. 15c). The result suggests that the NHS-activation of carboxylic acid groups at the liquid crystal interface does not perturb the orientation of liquid crystals. The inventors then replaced the NHS/EDC solution with 0.20 mM 17-amino acid oligopeptide solution in PBS (pH 7.6) and characterized the optical appearance of the liquid crystal by using polarized light microscopy (FIG. 15d). During 1.5 h of contact with the oligopeptide solution, the optical appearance of 5CB became bright and colorful. The bright image of 5CB indicates the anchoring transition of liquid crystals from homeotropic to tilted alignment. It appears that the structural strain inflicted by the 17-amino acid oligopeptide immobilized at the aqueous-liquid crystal interface could cause changes in the orientation of alkyl chains in the monolayer, leading to the orientational transition of liquid crystals to tilted alignment.

Figure 16:
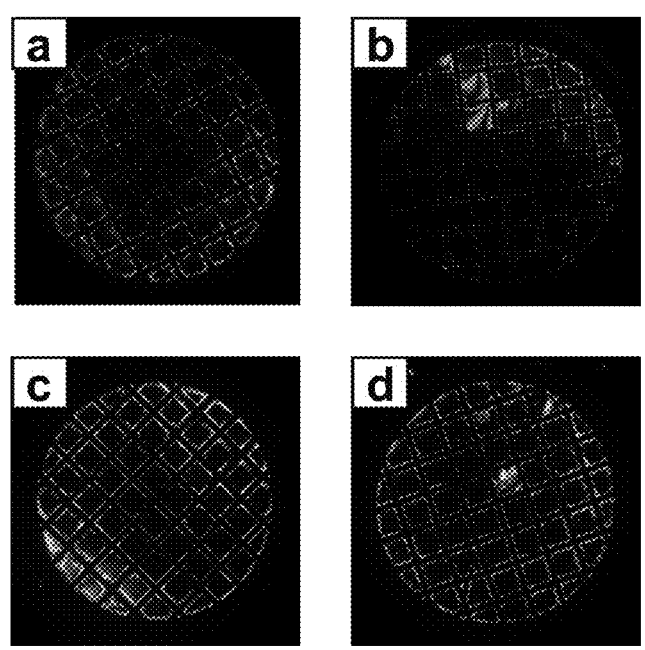
FIG. 16. Polarized light micrographs of (a) 5CB (crossed polars) laden with a mixture of carboxyl-/hydroxyl-terminated surfactants after 1.5 h contact with 17-amino acid oligopeptide. Polarized light micrographs of 5CB (crossed polars) laden with the NHS-activated mixed monolayer after 1.5 h of contact with (b) ethanolamine, (c) lysine, and (d) polylysine solution (PBS buffer, pH 7.6).

In order to understand the orientational response of liquid crystals to the immobilization of the 17-amino acid oligopeptide, the inventors carried out several control experiments. First, an aqueous solution of the 17-amino acid oligopeptide was introduced to the mixed monolayer consisting of OH— and CO$_2$H-terminated surfactants without NHS-activation of the carboxylic acid groups. Without NHS-activation, the primary amine groups of the oligopeptide cannot form covalent bonds with the surfactants. After 1.5 h of contact with the 17-amino acid oligopeptide, the optical appearance remained dark indicating homeotropic alignment of 5CB at the aqueous-liquid crystal interface (FIG. 16a). The result suggests that the orientation of 5CB is not perturbed without the formation of covalent bonds between the monolayer and the oligopeptide. Next, after the NHS activation of mixed monolayer, the inventors introduced three different compounds that commonly possess primary amine groups. The aqueous solution of in PBS (pH 7.6) was equilibrated with the NHS-activated monolayer for 1.5 h at rt. During incubation, the optical appearance of 5CB also remained homogeneously black (FIGS. 16b-d). Although the primary amine groups of ethanolamine, DL-lysine, and polylysine are likely to form covalent bonds with the NHS-activated carboxylic groups, the immobilization of those compounds did not perturb the anchoring of the liquid crystals. It therefore appears that the primary amine groups specifically constrained along the backbone are essential to cause changes in the structure of the mixed monolayer and thus the anchoring transition of liquid crystals.

Figure 17:
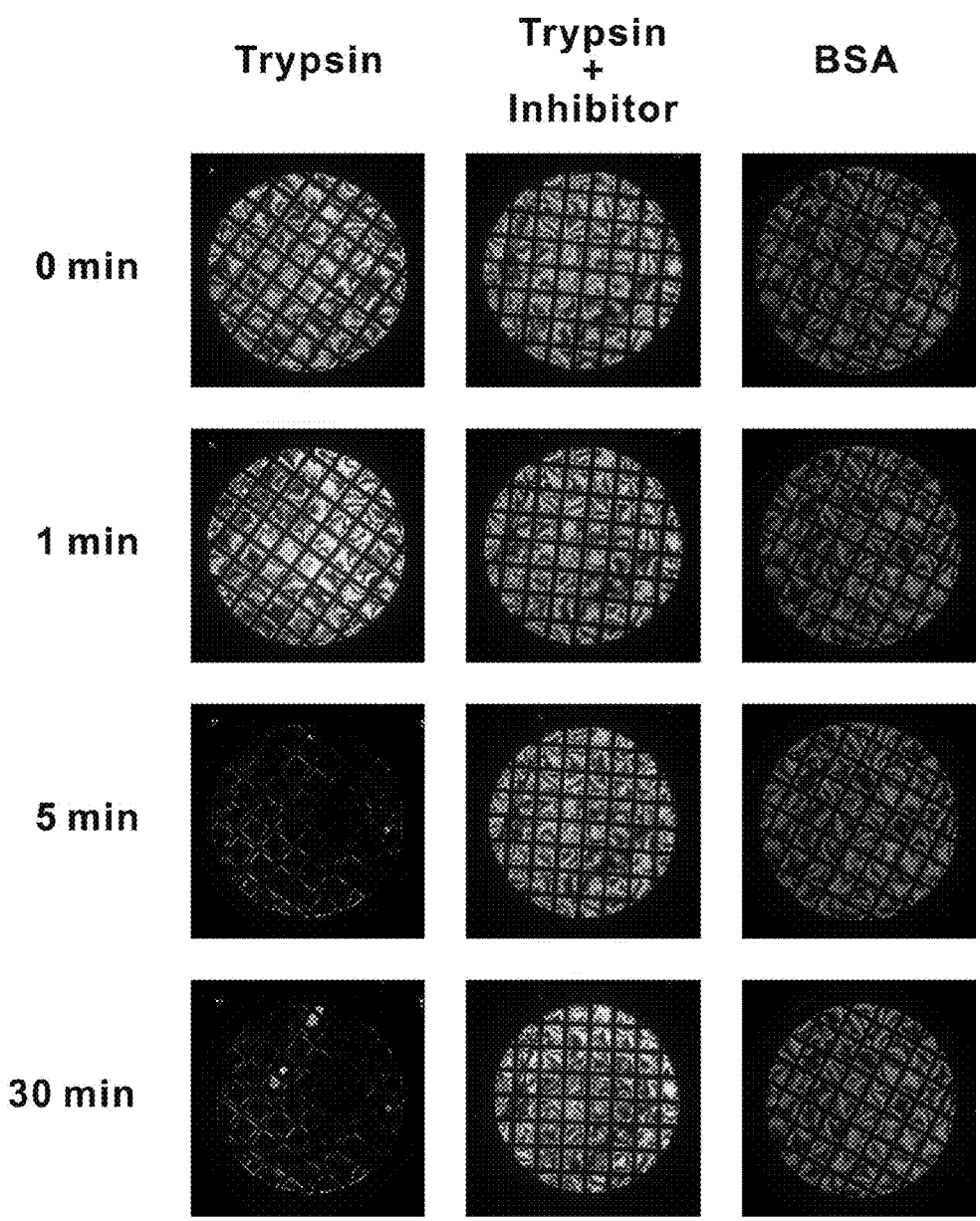
FIG. 17. Polarized light micrographs (crossed polars) of 5CB laden with the mixed monolayer modified with 17-amino acid oligopeptide after contacting with trypsin, a mixture of trypsin and trypsin inhibitor, or BSA solution in 30 mM HEPES buffer containing 20 mM $CaCl_2$ (pH 8.0) for the indicated time periods.

Selective Detection of Enzymatic Cleavage. The results of control experiments described above suggest that the tilted orientation of 5CB at the aqueous-liquid crystal interface is likely to be caused by structural strain introduced by the immobilized oligopeptides. It was therefore believed that the orientation of 5CB at the oligopeptide-immobilized interface could be altered by contacting with an enzyme that cleaves the oligopeptide substrate because the enzymatic cleavage can release the structural strain inflicted by the oligopeptide. Consequently, the inventors then used trypsin that can cleave the 17-amino acid oligopeptide at four different locations. Trypsin selectively cleaves peptide bonds after (on the C-terminal side of) lysine (K) and arginine (R). The optimum pH for trypsin is about 8, and the addition of moderate amounts of CaCl$_2$ (20 mM) can maximize the trypsin activity and stabilize the protease. The inventors therefore prepared a 200 nM trypsin solution in 30 mM HEPES buffer (pH 8.0) containing 20 mM CaCl$_2$ and introduced the solution to the oligopeptide-immobilized liquid crystal interface. Within 1 min of contact with the trypsin solution, the bright image of 5CB exhibited changes in the interference colors from red, green, and yellow to yellow and gray, indicating decrease in tilt (relative to the surface normal) of 5CB at the aqueous-5CB interface (FIG. 17). After 5 min of contact with the trypsin solution, the optical appearance of 5CB became homogeneously black indicating the anchoring transition of 5CB to homeotropic alignment. To prove the proposition that this orientational transition of 5CB could be caused by the enzymatic cleavage of the oligopeptides, the inventors used the trypsin-chymotrypsin inhibitor from *Glycine max* (Bowman-Birk inhibitor). Before the addition of trypsin solution to the sample, the trypsin-chymotrypsin inhibitor was added to the trypsin solution to give 1:2 weight ratio of trypsin to the inhibitor. After incubated for 10 min at rt, the aqueous solution of trypsin and inhibitor was introduced to the sample. In contrast to trypsin, the mixture of trypsin and the inhibitor did not show the orientational transition of 5CB to homeotropic alignment after 1 h of incubation (FIG. 17). The inventors also performed a control experiment with BSA that cannot cleave the 17-amino acid oligopeptide. BSA also did not exhibit the anchoring transition of 5CB (FIG. 17).

The results, as a whole, suggest that the orientational transition observed with trypsin treatment arises from the enzymatic cleavage of the oligopeptide rather than nonspecific binding or other interactions. Therefore, the immobilization of oligopeptides at aqueous-liquid crystal interface introduces structural strain into the monolayer, and the release of the structural strain by enzymatic cleavage could cause changes in monolayer structure and anchoring of liquid crystals. The strategy reported in this example can be used to selectively report enzymatic activities when an appropriate oligopeptide substrate is immobilized.

Example 6

Preparation of a device containing a polymerized membrane at the interface between a nematic liquid crystal and an aqueous phase—the polymerized membrane containing the antibody for botulinum neurotoxin.

This example describes the polymerization of antibodies with adipoyl chloride at interfaces between thermotropic liquid crystals and aqueous phases to facilitate the detection of botulinum neurotoxin according to the present invention. Specifically, antibodies against botulinum toxin are polymerized with adipoyl chloride as a cross linker at the interface between liquid crystals and aqueous phases. The adipoyl chloride is added to the liquid crystal 4-cyano-4'-pentylbiphenyl (5CB) and homogeneously mixed by sonication. The composition of the mixture is about 1.5 wt. % adipoyl chloride in 5CB. The mixture is deposited into the pores of gold TEM grids supported on octyltrichlorosilane (OTS)-coated glass slides. The antibody in PBS at a concentration of 1 micromolar is introduced to the sample. After polymerization for 2 hours at room temperature, the antibody solution is removed and the sample is rinsed with a slightly basic water (pH 8) more than five times. Thusly prepared, a sample containing botulinum toxin may now be introduced to the polymerized antibody at the aqueous phase/LC interface to facilitate detection of the toxin by a change in orientation of the LC.

Example 7

Preparation of a device containing a polymerized membrane at the interface between a nematic liquid crystal and an aqueous phase—the polymerized membrane containing the phospholipase $A_2$ substrate stearoyl-2-acyl-3-sn-glycerophosphorylethanolamine.

This example describes the polymerization of substrates for phospholipase $A_2$ with adipoyl chloride at interfaces between thermotropic liquid crystals and aqueous phases. The substrate is polymerized with adipoyl chloride as a cross linker at the interface between liquid crystals and aqueous phases. The adipoyl chloride is added to the liquid crystal 4-cyano-4'-pentylbiphenyl (5CB) and homogeneously mixed by sonication. The composition of the mixture is about 1.5 wt. % adipoyl chloride in 5CB. The mixture is deposited into the pores of gold TEM grids supported on octyltrichlorosilane (OTS)-coated glass slides. Stearoyl-2-acyl-3-sn-glycerophosphorylethanolamine at a concentration of 1 millimolar is introduced and, after polymerization for 2 hours at room temperature, the stearoyl-2-acyl-3-sn-glycerophosphorylethanolamine solution is removed and the sample is rinsed with a slightly basic water (pH 8) more than five times. Thusly prepared, a sample containing an enzyme having phospholipase $A_2$ activity may now be introduced to the polymerized tearoyl-2-acyl-3-sn-glycerophosphorylethanolamine at the aqueous phase/LC interface to facilitate detection of the enzyme by a change in orientation of the LC (described further in Example 9).

Example 8

Selective detection of antibody for botulinum neurotoxin.

A polymerized membrane of botulinum neurotoxin is prepared at the aqueous-5CB interface by addition of 1 micromolar botulinum neurotoxin to the aqueous phase, and adipoyl chloride to the liquid crystal. Following polymerization of botulinum neurotoxin, the aqueous solution is replaced by a solution containing antibodies to botulinum neurotoxin. After binding of the antibodies to the polymerized membrane of botulinum neurotoxin, DLPC is added to the aqueous phase containing the antibodies. To a second aqueous phase contacting a botulinum neurotoxin membrane/liquid crystal that has not been contacted with a sample, DLPC is also added. The time at which the order of the LC changes following addition DLPC is different in the presence/absence of the antibody, thus allowing the presence of antibody in a sample to be detected.

Example 9

Selective detection of phospholipase $A_2$ (PLA2) activity enzymatic cleavage.

A membrane containing a polymerized substrate for PLA2 is prepared as described in example 7. A sample containing PLA2 and calcium ions is added to the aqueous phase and incubated against the membrane. Observation of the optical appearance of the liquid crystal reveals a change in order of the liquid crystal in the presence of the PLA2. In a control experiment, PLA2 is added to the aqueous solution in the absence of Ca2+ ions but in the presence of EDTA. In this experiment, there is no observable change in the optical appearance of the liquid crystal. This example demonstrates the use of the invention to detect the enzymatic activity of PLA2 using a cross-linked membrane containing a substrate for PLA2.

Those skilled in the art will recognize, or be able to ascertain using no more than routine experimentation, numerous equivalents to the specific materials and methods described herein. Such equivalents are considered to be within the scope of this invention and encompassed by the following claims.

What is claimed is:

1. A method for detecting the presence of a bioagent in a sample, comprising:
   (a) forming a membrane containing a polymerized target for the bioagent at an interface between a liquid crystal and an aqueous phase, said polymerized target comprising the target for the bioagent covalently cross-linked to a polymer network;
   (b) introducing the sample into the aqueous phase; and
   (c) observing the orientational order of the liquid crystal, thereby detecting the presence of the bioagent in the sample, wherein interaction of the bioagent and said polymerized target leads to a change in the orientational order of the liquid crystal, said orientational change indicating the presence of the bioagent.

2. The method according to claim 1 wherein said bioagent is an enzyme and the target is a substrate for the enzyme.

3. The method according to claim 1 wherein said bioagent is an antibody and the target is an antigen recognized by said antibody.

4. The method according to claim 1 wherein said bioagent is an antigen and the target is an antibody that recognizes said antigen.

5. The method according to claim 1 wherein the polymer network comprises a non-target molecule that is cross-linked to said target.

6. The method according to claim 1 wherein said membrane is further comprised by an adsorbed or deposited layer of non-target molecules.

7. The method according to claim 1 wherein said aqueous phase includes an enhancing agent that enhances the change in orientation of the liquid crystal upon interaction of the bioagent and target.

8. The method according to claim 7 wherein the enhancing agent is L-a-dilauroyl phosphatidylcholine (L-DLPC).

* * * * *

UNITED STATES PATENT AND TRADEMARK OFFICE
CERTIFICATE OF CORRECTION

PATENT NO.       : 8,329,423 B2                                    Page 1 of 1
APPLICATION NO.  : 13/011514
DATED            : December 11, 2012
INVENTOR(S)      : Abbott et al.

It is certified that error appears in the above-identified patent and that said Letters Patent is hereby corrected as shown below:

Column 1, line 19, "N00014-14-04-1-0659" should be -- N00014-04-1-0659 --.

Signed and Sealed this
Nineteenth Day of February, 2013

Teresa Stanek Rea
*Acting Director of the United States Patent and Trademark Office*

SEQUENCE LISTING

<160> NUMBER OF SEQ ID NOS: 3

<210> SEQ ID NO 1
<211> LENGTH: 206
<212> TYPE: PRT
<213> ORGANISM: Homo sapiens

<400> SEQUENCE: 1

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 2
<211> LENGTH: 19
<212> TYPE: PRT
<213> ORGANISM: Artificial
<220> FEATURE:
<223> OTHER INFORMATION: The leucine indicated a position 17 is a
      norleucine. This peptide also includes an aminde group at its C
      terminus. The source of this sequence is human SNAP-25.

<400> SEQUENCE: 2

```
Cys Ser Asn Lys Thr Arg Ile Asp Glu Ala Asn Gln Arg Ala Thr Lys
1               5                   10                  15

Leu Leu Cys
```

<210> SEQ ID NO 3
<211> LENGTH: 17
<212> TYPE: PRT
<213> ORGANISM: Artificial
<220> FEATURE:
<223> OTHER INFORMATION: The leucine indicated at position 16 is a
      norleucine. This peptide also includes an amide group at its C
      terminus. The source of this sequence is human SNAP-25.

<400> SEQUENCE: 3

```
Ser Asn Lys Thr Arg Ile Asp Glu Ala Asn Gln Arg Ala Thr Lys Leu
1               5                   10                  15
Leu
```